United States Patent [19]

Collington et al.

[11] 4,342,756

[45] Aug. 3, 1982

[54] AMINOCYCLOPENTANE ALKENOIC ACIDS AND ESTERS AND PHARMACEUTICAL COMPOSITIONS

[75] Inventors: Eric W. Collington, Welwyn; Peter Hallett, Buntingford; Christopher J. Wallis, Royston; John Bradshaw, Ware; Norman F. Hayes, Hitchin, all of England

[73] Assignee: Glaxo Group Limited, England

[21] Appl. No.: 258,721

[22] Filed: Apr. 29, 1981

[30] Foreign Application Priority Data

Apr. 30, 1980 [GB] United Kingdom ............... 8014256

[51] Int. Cl.³ ............... A61K 31/54; A61K 31/535; C07D 295/14

[52] U.S. Cl. ............... 424/244; 544/163; 544/165; 424/246; 544/162; 544/169; 424/248.5; 544/171; 544/357; 424/248.51; 544/360; 544/372; 424/248.52; 544/379; 544/393; 424/248.53; 544/395; 544/399; 424/248.54; 544/400; 546/187; 424/248.55; 546/190; 546/205; 424/250; 546/208; 546/213; 424/267; 546/230; 546/233; 424/274; 546/234; 546/235; 424/45; 546/238; 546/239; 542/426; 260/239 BF; 260/243.3; 544/58.1; 260/244.4; 260/245.7; 544/58.2; 260/330.3; 260/330.6; 544/58.6; 544/58.7; 544/79; 544/82; 544/85; 544/86; 544/87; 544/107; 544/109; 544/110; 544/111; 544/121; 544/130; 544/141; 544/146; 544/158; 544/159

[58] Field of Search ............... 544/58.2, 58.6, 58.7, 544/58.1, 85, 86, 87, 79, 82, 107, 109, 110, 111, 121, 130, 141, 146, 158, 159, 163, 165, 169, 162, 171, 357, 360, 372, 379, 393, 395, 399, 400; 546/187, 190, 205, 208, 213, 230, 233, 234, 235, 238, 239; 260/243.3, 244.4, 245.7, 326.25, 326.35, 326.4, 239 BF, 330.3, 333; 542/426; 424/244, 246, 248.5, 248.53, 248.51, 248.52, 248.55, 250, 267, 274, 45

[56] References Cited

U.S. PATENT DOCUMENTS 4,182,903  1/1980  Favara et al. ............... 562/503
4,189,606  2/1980  Favara et al. ............... 562/455
4,239,778  12/1980 Venton et al. ............... 424/305
4,265,891  5/1981  Collington et al. ............... 424/244

OTHER PUBLICATIONS

Orth et al, *Topics in Current Chemistry*, 72 (1977) pp. 51-97.
LeBreton, *Proc. Natl. Acad. Sci. USA*, 76 (1979) pp. 4097-4100.

Primary Examiner—Robert W. Ramsuer
Attorney, Agent, or Firm—Bernard, Rothwell & Brown

[57] ABSTRACT

Compounds are described of the formula

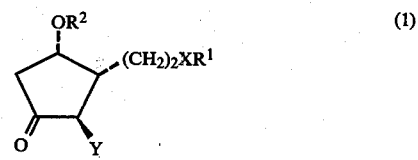

(1)

(and their salts and solvates) in which:

X is cis or trans —CH═CH—;

$R^1$ is $C_{1-7}$ alkyl terminated by —COOR$^3$ where $R^3$ is H, $C_{1-6}$ alkyl or $C_{7-10}$ aralkyl;

Y is a saturated heterocyclic amino group having 5–8 ring members; and $R^2$ is $C_{2-4}$ alkanoyl, $C_{3-6}$ alkenyl (optionally substituted), $C_{1-12}$ alkyl, or substituted or unsubstituted phenylalkyl, biphenylalkyl or naphthylalkyl.

These compounds inhibit blood platelet aggregation and bronchoconstriction and may be formulated for use as antithrombotic and anti-asthmatic agents.

14 Claims, No Drawings

AMINOCYCLOPENTANE ALKENOIC ACIDS AND ESTERS AND PHARMACEUTICAL COMPOSITIONS

The endoperoxides prostaglandins $G_2$ and $H_2$, and thromboxane $A_2$ are naturally occurring, reactive metabolites of arachidonic acid in human platelets. They are not only potent aggregatory agents but are also constrictors of vascular and bronchial smooth muscle, and therefore substances which antagonise their effects are of considerable interest in human medicine.

We have now found a new group of compounds which have shown endoperoxide and thromboxane antagonist activity, and are therefore of interest in the treatment of asthma and cardiovascular diseases. These compounds can broadly be described as cyclopentanealkenoic acids and esters in which the double bond is in the 3,4-position in relation to the cyclopentane ring and in which the ring is substituted by heterocyclic amino, oxo and alkanoyloxy or ether (particularly aralkoxy) groups.

The invention thus provides compounds of the general formula (1)

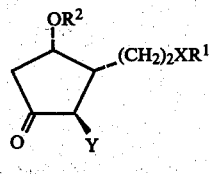
(1)

wherein
X is cis or trans $-CH=CH-$;
$R^1$ is straight or branched $C_{1-7}$ alkyl bearing as a terminal substituent $-COOR^3$ where $R^3$ is a hydrogen atom, $C_{1-6}$ alkyl or $C_{7-10}$ aralkyl (e.g. benzyl);
Y represents a saturated heterocyclic amino group which has 5-8 ring members and (a) optionally contains in the ring $-O-$, $-S-$, $-SO_2-$, $-NR^4$ (where $R^4$ is a hydrogen atom, $C_{1-7}$ alkyl or aralkyl having a $C_{1-4}$ alkyl portion); and/or (b) is optionally substituted by one or more $C_{1-4}$ alkyl groups;
$R^2$ is (i) $C_{2-4}$ alkanoyl; (ii) $C_{3-6}$ alkenyl, optionally substituted by phenyl (the phenyl being optionally substituted by $C_{1-4}$ alkyl, $C_{1-4}$ alkoxy, halogen, $C_{5-7}$ cycloalkyl or phenyl $(C_{1-4})$ alkyl), biphenyl (optionally substituted by $C_{1-4}$ alkyl, $C_{1-4}$ alkoxy or halogen), or naphthyl; (iii) $C_{1-12}$ alkyl; (iv) $C_{1-5}$ alkyl substituted by (a) phenyl [optionally substituted by halogen, hydroxy, $C_{1-6}$ alkyl, $C_{1-6}$ alkoxy, $C_{1-4}$ hydroxyalkoxy, trifluoromethyl, cyano, aryloxy (e.g. phenoxy), $C_{5-7}$ cycloalkyl, aralkoxy (e.g. benzyloxy), dimethylaminomethyl, carboxamido ($-CONH_2$), thiocarboxamido ($-CSNH_2$), $C_{1-4}$ alkanoyl, $-NR^5R^6$ (where $R^5$ and $R^6$ are the same or different and are each a hydrogen atom or $C_{1-4}$ alkyl, or where $-NR^5R^6$ is a saturated heterocyclic amino group as defined above for Y), $C_{1-3}$ alkylthio, $C_{1-3}$ alkylsulphinyl, $C_{1-3}$ alkylsulphonyl, phenylalkyl having a $C_{1-3}$ alkyl portion, aminosulphonyl, $C_{1-3}$ alkanoylaminosulphonyl, phenylsulphonyl (the phenyl portion being optionally substituted by $C_{1-3}$ alkyl or $C_{1-3}$ alkoxy), nitro, or thienyl], (b) biphenyl (optionally substituted by phenyl or one or two $C_{1-4}$ alkyl, $C_{1-4}$ alkoxy or halogen substituents), or (c) naphthyl (optionally substituted by $C_{1-4}$ alkyl, $C_{1-4}$ alkoxy or halogen);
and the physiologically acceptable salts and the solvates (e.g. hydrates) thereof.

The structural formulae herein are to be understood to include the enantiomers of each of the compounds concerned as well as mixtures of the enantiomers, including racemates, even though the precise structure as set out only relates to one enantiomer.

The alkyl groups referred to above in the definition of the compounds of formula (1) may be straight or branched.

The alkyl portion of the group $R^1$ may for example contain 1-5 carbon atoms in a straight or branched chain, and is preferably $-CH_2CH_2-$. Examples of suitable $R^3$ groups are $C_{1-3}$ alkyl (e.g. methyl), but $R^3$ is preferably a hydrogen atom. $R^1$ is thus preferably $-(CH_2)_2COOH$.

When $R^3$ is a hydrogen atom, the compounds are capable of salt formation with bases and the compounds are preferably used in the form of such salts. Examples of suitable salts are alkali metal (e.g. sodium and potassium), alkaline earth metal (e.g. calcium or magnesium), ammonium, substituted ammonium (e.g. tromethamine or dimethylaminoethanol), piperazine, N,N-dimethylpiperazine, morpholine, piperidine and tertiary amino (e.g. triethylamine) salts. Inorganic salts are preferred.

X is preferably a cis $-CH=CH-$ group.

The heterocyclic amino group Y may for example have a 5, 6 or 7-membered ring, e.g. pyrrolidino, piperidino, morpholino, piperazino, thiamorpholino, 1-dioxothiamorpholino, homomorpholino and hexamethyleneimino. Examples of the optional substituents which may be present on a second nitrogen atom in the ring are methyl, ethyl and benzyl. The carbon atoms of the heterocylic rings may for example be substituted by methyl or ethyl. Y is preferably piperidino, morpholino, homomorpholino, thiamorpholino or 1-dioxothiamorpholino, and compounds in which Y is a morpholino or piperidino group are particularly preferred.

The amino group Y enables the compounds to form salts with organic acids, e.g. maleates.

$R^2$ may for example be $C_{5-10}$ alkyl (e.g. pentyl or decyl); $C_{3-5}$ alkenyl (e.g. allyl, optionally substituted by phenyl); or $C_{1-5}$ alkyl (e.g. methyl or propyl) substituted by phenyl [optionally substituted by a $C_{1-4}$ alkyl (e.g. tert butyl), $C_{5-7}$ cycloalkyl (e.g. cyclohexyl), $C_{1-3}$ alkylthio (e.g. methylthio), phenyl $(C_{1-3})$ alkyl (e.g. benzyl) or thienyl], biphenyl [optionally substituted by $C_{1-3}$ alkyl (e.g. methyl), $C_{1-3}$ alkoxy (e.g. methoxy), halogen (e.g. chlorine) or phenyl], or naphthyl.

$R^2$ is preferably a phenylalkyl group in which the alkyl portion contains $C_{1-3}$ carbon atoms and the phenyl is substituted with one of the following groups: $C_{1-3}$ alkylthio, thienyl or phenyl optionally substituted by $C_{1-3}$ alkyl, $C_{1-3}$ alkoxy; halogen or phenyl; or cinnamyl.

Particularly preferred $R^2$ groups are phenylalkyl groups in which the alkyl portion is a $C_{1-3}$ alkylene chain and the phenyl group carries a phenyl substituent, preferably in the para-position (which phenyl substituent is optionally substituted by a $C_{1-3}$ alkyl, $C_{1-3}$ alkoxy or halogen, this additional substituent preferably being in the meta or more particularly the para-position); or cinnamyl.

A particularly preferred group of compounds has the formula (1) in which:
X is cis $-CH=CH-$,
$R^1$ is $-CH_2CH_2COOH$, Y is morpholino or piperidino, and R² is phenyl ($C_{1-3}$) alkyl in which the phenyl group is substituted by phenyl (which phenyl substituent is optionally substituted by $C_{1-3}$ alkyl, $C_{1-3}$ alkoxy or halogen); or cinnamyl.

and the physiologically acceptable salts and solvates (e.g. hydrates) thereof.

Particularly important compounds in this latter group are those in which Y is morpholino and R² is 1,1'-biphenylmethyl; 1,1'-biphenylmethyl substituted in the para-position by methyl, methoxy or chloro or in the meta-position by methoxy; 1,1'-biphenylpropyl; or cinnamyl; and those in which Y is piperidino and R² is 1,1'-biphenylmethyl or 4'-methoxy-1,1'-biphenylmethyl. Especially important are:

[1α(Z), 2β,5α]-(±)-7-[5-[[(1,1'-biphenyl)-4-yl]methoxy]-2-(4-morpholinyl)-3-oxocyclopentyl]-4-heptenoic acid; and

[1R-[1α(Z),2β,5α]]-(−)-7-[5-[[(1,1'-biphenyl)-4-yl]methoxy]-2-(4-morpholinyl)-3-oxocyclopentyl]-4-heptenoic acid; and the hydrates and salts thereof, particularly the calcium, piperidine, piperazine and N,N-dimethylpiperazine salts. The calcium salts are particularly important.

In general, compounds of formula (1) in which the carbon atom carrying the —(CH₂)₂XR¹ group is in the R-configuration (and mixtures containing this isomer) are preferred.

Compounds of formula (1) inhibit blood platelet aggregation and bronchoconstriction. The test for inhibition of platelet aggregation is as described by G. V. Born in Nature 194, 927–929 (1962) except in that collagen is used instead of ADP as the pro-aggregatory agent. The test for potential inhibition of bronchoconstriction is as described by K. M. Lulich et al in British Journal of Pharmacology 58, 71–79, (1976) except guinea-pig lung is used instead of cat lung.

The compounds are thus of interest in the treatment of asthma, and as inhibitors of platelet aggregation and thrombosis for use in renal dialysis and the treatment and prevention of occlusive vascular diseases such as arteriosclerosis, atherosclerosis, peripheral vascular disease, cerebral vascular disease including transient ischaemic attacks, stroke, pulmonary embolism, diabetic, retinopathy, post operative thrombosis, angina and myocardial infarction. They may be formulated in conventional manner for use, with one or more pharmaceutical carriers.

For oral administration, the pharmaceutical composition may take the form of, for example, tablets, capsules, powders, solutions, syrups, or suspensions prepared by conventional means with acceptable excipients.

The compounds may be formulated for parenteral administration by bolus injections or continuous infusion. Formulations for injections may be presented in unit dosage form in ampoules, or in multi-dose containers, which an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution before use with a suitable vehicle, e.g. sterile pyrogen-free water.

For administration by inhalation the compounds are conveniently delivered in the form of an aerosol spray presentation from pressurised packs or a nebuliser, or as a cartridge from which the powdered composition may be inhaled with the aid of a suitable device. In the case of a pressurised aerosol the dosage unit may be determined by providing a valve to deliver a metered amount.

For use as antithrombotic agents, the compounds are preferably administered orally, for example in amounts of 0.05 to 10 mg/kg body weight, 1 to 4 times daily.

For use in the treatment of asthma, the compounds may also be administered orally in amounts of 0.05 to 10 mg/kg body weight, 1 to 4 times daily; preferably however they are administered by inhalation at doses varying from 0.3 to 30 mg, 1 to 4 times daily. The compounds may be used in combination with other antiasthmatic agents.

The precise dose administered will of course depend on the age and condition of the patent.

Suitable methods for preparing compounds of formula (1) are described below.

In the following discussion, the groups R¹, R², R³, X and Y are as defined above except where otherwise indicated.

(a) Compounds of formula (1) may be prepared by oxidising a corresponding hydroxy compound, e.g. a compound of formula (2)

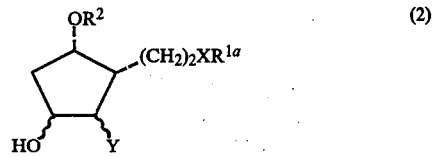

(2)

(wherein $R^{1a}$ is $C_{1-7}$ alkyl substituted by —COOR³, —CH₂OH or —CHO).

Suitable methods of oxidation include using a $Cr^{VI}$ oxidising reagent in a suitable solvent, e.g. chromic acid in acetone (e.g. Jones reagent, preferably used in the presence of a diatomaceous silica such as Celite) or CrO₃ in pyridine. These reagents are for example used at temperatures of −20° to room temperature.

Other important methods include using an activated sulphur reagent, e.g. (i) N-chlorosuccinimidedimethylsulphide complex in a suitable solvent (e.g. toluene or dichloromethane) at temperatures of for example −25° to 25°, preferably at 0°–5°, (ii) a dialkylsulphoxide (e.g. dimethylsulphoxide) activated by a suitable electrophilic reagent (such as oxalyl chloride, acetyl bromide or thionyl chloride) in a suitable solvent (e.g. toluene or dichloromethane), e.g. at −70° to −20°; dicyclohexylcarbodiimide can also be used as the electrophilic reagent (preferably in the presence of CF₃COOH or its pyridinium salt) at for example −10° to room temperature, using the same solvents, or (iii) pyridine, —SO₃ complex in dimethylsulphoxide, preferably at 0° to room temperature.

When R³ is a hydrogen atom, better yields are sometimes obtained by prior protection of the carboxyl group, for example in the form of a trialkyl (e.g. trimethyl, triethyl or dimethyl(1,1-dimethylethyl))silyl ester.

$Cr^{VI}$ oxidising agents are generally preferred. The choice of oxidation method however will depend on the nature of the starting material of formula (2). Thus when $R^{1a}$ is —CH₂OH or —CHO, a $Cr^{VI}$ oxidising agent will generally be used. When Y is in the α-configuration conditions should be chosen to effect epimerisation, either at the same time or after oxidation.

Any hydroxy or amino group present in the starting material and required in the end product should be suitably protected in this reaction.

(b) Compounds of formula (1) in which $R^3$ is an alkyl or aralkyl group can be prepared by esterification of the corresponding carboxylic acid in which $R^3$ is a hydrogen atom, reaction with a diazoalkane being preferred.

Alternatively, the acid may be converted into an activated derivative (e.g. a corresponding mixed anhydride) e.g. by reaction with an alkyl chloroformate (e.g. isobutyl chloroformate) in the presence of a suitable base, e.g. triethylamine or pyridine. The activated derivative can then be reacted with an appropriate alcohol, for example using a solvent such as acetone and temperatures of $-10°$ to room temperature.

(c) Compounds of formula (1) in which $R^2$ is phenalkyl substituted by amino may be prepared by reduction of the corresponding azide, for example using zinc and sodium dihydrogen phosphate (e.g. in tetrahydrofuran).

(d) Compounds of formula (1) may also be prepared by selective reduction of a corresponding compound of formula (1) in which X is an acetylene group. These intermediates are also novel compounds. Suitable methods of reduction include using hydrogen in the presence of a catalyst, e.g. palladium on a support (e.g. $CaCO_3$ or $BaSO_4$) and poisoned for example by lead or pyridine Suitable solvents include ethyl acetate or methanol.

(e) Where salts of compounds of formula (1) are desired such salts may be formed by conventional methods, for example by treating acids of formula (1) with appropriate bases. Salts may also be formed with acids.

The salts may be formed in conventional manner. For example, amine salts are conveniently prepared by adding the amine to a solution of an acid of formula (1) in a solvent such as ether. Salts of inorganic bases may be prepared by adding the base to a solution of the acid in an aqueous organic solvent. Certain salts may also be prepared by exchange of cation; for example, calcium salts may be prepared by addition of a calcium salt (e.g. the chloride or acetate) to a solution of a salt of a compound of formula (1), e.g. an amine or alkali metal salt.

The principal intermediates required for the reactions described above may be prepared by the following methods.

It will be appreciated that the following reactions will frequently require the use of, or will conveniently be applied to, starting materials having protected functional groups. It is to be understood generally that the references below to specific starting materials are intended to include references to corresponding materials having protected functional groups.

It will also be appreciated that certain of the reactions described below are capable of affecting other groups in the starting material which are desired in the end product, and account must be taken of this when performing multi-stage reactions.

(f) Compounds of formula (3)

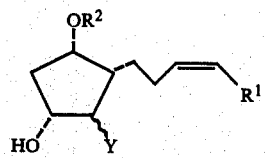

(where $R^1$ is as defined above for $R^1$ where $R^3$ is a hydrogen atom) may be prepared by reacting a compound of formula (4)

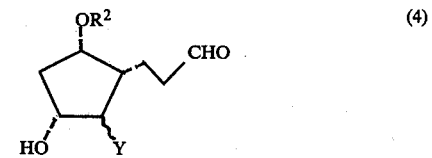

with an appropriate Wittig reagent, e.g. a phosporane of formula $R_3^7P=CHR^1$ (where $R^7$ is $C_{1-6}$ alkyl or aryl, e.g. monocyclic aryl such as phenyl) or a salt thereof, e.g. the potassium salt. Suitable reaction solvents include hydrocarbons (e.g. benzene and toluene), ethers (e.g. tetrahydrofuran), dialkylsulphoxides (e.g. dimethylsulphoxide), alcohols and halogenated hydrocarbons. The reaction may be carried out at any suitable temperature from $-70°$ to $50°$ C. preferably at room temperature.

The reaction is particularly suitable for the preparation of compounds in which $R^1$ is terminally substituted by $-COOH$ (in salt form). Any hydroxy group present is preferably in a protected state prior to this reaction. Suitable hydroxyl protecting groups are described below. Any $-NH_2$ group present should also be protected, e.g. by t-butoxycarbonyl.

If desired, the configuration of the group X and $R^1$ and $R^2$ may then be modified to provide other compounds of formula (2) e.g. by methods (1)–(0) below or (b) or (c) above.

The starting materials of formula (4) may be prepared by the following sequence:

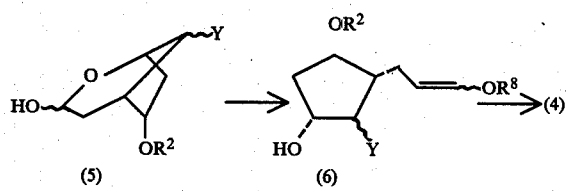

A lactol of formula (5) is treated with an appropriate Wittig reagent (e.g. $R_3^7P=CHOR^8$, where $R^7$ is as defined above and $R^8$ is $C_{1-4}$ alkyl) to give the vinyl ether (6). The reactions may be performed as described for process (f). The vinyl ether (6) is then hydrolysed to give the aldehyde (4), for example using a dilute acid such as hydrochloric acid. Acetone is a suitable solvent.

Lactols of the formula (7)

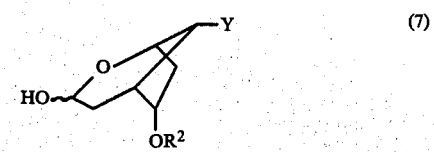

may be prepared by the method described in British Patent Specification No. 2028805A, using starting materials containing the appropriate $R^2$ group.

Lactols of formula (8)

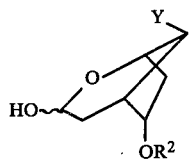

required as starting materials may be prepared by the following sequence:

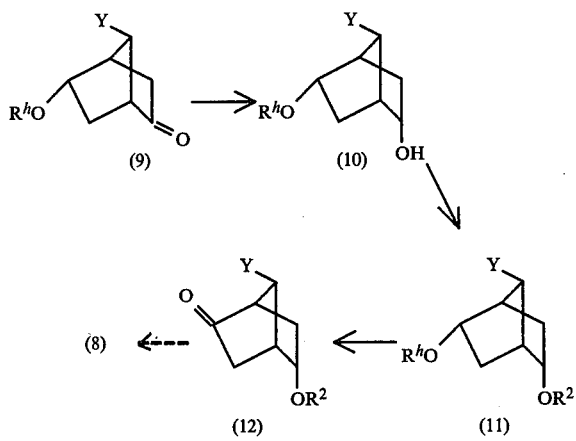

($R^h$ above represents a hydroxyl protecting group) Thus the norbornanone (9) is first reduced (e.g. with $NaBH_4$) to the alcohol (10) into which the $R^2$ group is then introduced (e.g. by reaction with $R^2L$, where L is a leaving group, e.g. halogen or tosylate) to give the compound (11). The protecting group ($R^h$) is then removed and the hydroxy group oxidised (e.g. as described for process (a)) to give the norbornanone (12). The latter can then be converted into the lactol (8) by Baeyer-Villiger oxidation followed by reduction (e.g. with di-isobutyl aluminium hydride).

(g) Compounds of formula (2) in which the groups Y and OH are both in the β-position may be prepared by reducing the corresponding compound of formula (1), e.g. with lithium tri-sec-butyl borohydride.

(h) Compounds of formula (2) in which $R^{1a}$ contains —$CH_2OH$ may be prepared by reducing the corresponding acid or ester of formula (2) or (1), e.g. with $LiAlH_4$.

(j) Compounds of formula (2) in which $R^{1a}$ contains —CHO may be prepared in the same manner as generally described for process (f) by reacting a compound of formula (4) with a phosphorane of formula $R_3^7P=CHR^{1a}$ in which $R^{1a}$ is $C_{1-7}$ alkyl substituted by a protected formyl group (e.g. acetal). Removal of the protecting group then gives the required formyl intermediate.

(k) Compounds of formula (2) in which Y is in the α-configuration and the ring hydroxy group is in the β-configuration may be prepared by epimerising the corresponding compound in which the ring hydroxy group is in the α-position. This may for example be effected with triphenylphosphine in the presence of an acid (e.g. formic or benzoic acid) and $(C_2H_5OOC.N)_2$ at a low temperature. Tetrahydrofuran is a suitable solvent.

(l) The acetylenes required as starting materials for process (d) may be prepared by first reacting a compound of formula (7) with a Wittig reagent $(R_3^7P=CBrR^1)$, as described above for process (f). The product is then dehydrobrominated to form the side chain acetylene group, and the ring hydroxy group then oxidised, as described for process (a).

(m) Compounds of formula (2) in which X is trans —CH=CH— may be prepared by isomerising the corresponding cis compound. The isomerisation may for example be effected by treatment with, for example, p-toluene sulphinic acid in dioxan (e.g. at reflux) or azobisisobutyronitrile and thiophenol, using for example a hydrocarbon solvent (e.g. benzene) and any suitable temperature up to reflux.

(n) Compounds of formula (2) in which $R^2$ is phenalkyl substituted by —$CH_2N(CH_3)_2$ may be prepared by treatment of the corresponding formyl compound with dimethylamine in the presence of a reducing agent, e.g. sodium cyano borohydride. The starting materials for this reaction may be made by the general method (f).

(o) Compounds of formula (2) in which $R^2$ is phenalkyl substituted by —$CONH_2$ or —$CSNH_2$ and $R^3$ is hydrogen may be prepared from the corresponding cyano compound by hydrolysis or hydrosulphidation, e.g. with sulphur in the presence of a reducing agent.

(p) Compounds of formula (2) in which $R^2$ is phenalkyl substituted by alkylsulphinyl or alkylsulphonyl may be prepared by oxidation of the corresponding alkylthio compound with a peracid, for example peracetic acid at room temperature.

(q) Compounds of formula (3) in which —$OR^2$ is an ether group and Y is in the β-configuration may be prepared by etherification of the corresponding hydroxy compound in which $R^2$ is a hydrogen atom. The reaction may for example be performed with an appropriate reagent $R^2L$ (L is as defined above), for example by reaction at room temperature in the presence of a suitable base (e.g. sodium hydride) in a suitable solvent (e.g. dimethylformamide).

(r) Compounds of formula (3) in which $R^2$ is an alkanoyl group and Y is in the β-configuration may be prepared by acylation of the corresponding hydroxy compound, for example with the appropriate alkanoic acid or an anhydride or halide thereof.

Any other hydroxy group present in the starting material used in process (q) or (r) should be protected in this reaction, as should the —COOH group in compounds in which $R^3$ is a hydrogen atom.

Suitable starting materials of formula (16) for processes (q) and (r) above may be prepared by the following sequence:

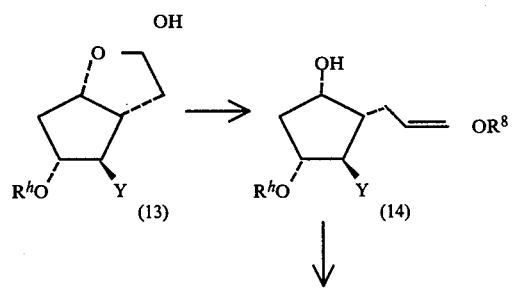

A lactol of formula (13), in which —OR$^h$ is a protected hydroxy group is first treated with a Wittig reagent to give the vinyl ether (14), which is then converted into the aldehyde (15) by treatment with mercuric acetate. These steps are performed in the same general way as for the preparation of compounds of formula (4). The compound of formula (16) may then be formed from the aldehyde (15) by the method of process (f).

The preparation of the lactols (13) is described in British Patent Specification No. 2028805A.

As an alternative to the formation of the ether group by process (q), it may be formed at an earlier stage, by etherification of the compound of formula (14).

(s) Compounds of formula (2) may also be prepared by modifying the corresponding compound in which Y is —NH$_2$.

This reaction may be performed by treating the starting material with a compound of the formula ZR$^9$Z, where Z is a readily displaceable group (such as halo, e.g. iodo, or hydrocarbylsulphonyloxy, e.g. p-toluenesulphonyloxy) and R$^9$ is the appropriate divalent group (e.g. —(CH$_2$)$_2$S(CH$_2$)$_2$—). The reaction may be carried out in a solvent such as acetonitrile or methanol at reflux, in the presence of a suitable base, e.g. potassium carbonate or sodium bicarbonate.

The amines required as starting materials for process (s) may be prepared by reduction of the corresponding azide, for example as described for process (c).

The azide starting materials may be prepared by methods analogous to those for preparing the compounds of formula (3), using reagents in which Y is an azido group. In particular, the preparations of lactols of formula (7) in which Y is azido is described in British Patent Specification No. 2028805A.

If desired, modification of the group R$^1$ or the configuration of the double bond may be effected before the formation of the group Y by process (s). The amino group may need to be protected in such transformations.

In the preparation of the intermediates the ring hydroxy group will often be protected and the liberation of this (or any other hydroxy group present) will frequently be the last step in the preparation. Conventional methods of protection may be used, protection in the form of dimethyl-1,1-dimethylethyl-silyloxy or tetrahydropyranyloxy groups being preferred. These groups may be removed by acid hydrolysis. Hydroxy groups may also be protected in the form of alkanoyloxy groups having up to 7 carbon atoms, e.g. acetoxy. These groups may be removed by alkaline hydrolysis.

When a specific enantiomer of formula (1) is required, intermediates having the required stereochemical configuration should be used in the above processes. For example, enantiomeric bromohydrin (17)

can be prepared by the method described by Newton et al in J.C.S. Chem. Comm., 1979, 908. This can then be converted into a compound of formula (1) in which the carbon atom carrying the -(CH$_2$)$_2$XR$^1$ group is in the (R)-configuration, via the appropriate enantiomer of the lactol (7), using the methods described above.

The following examples illustrate the invention. "Jones reagent" is a solution of chromic acid and sulphuric acid in water. A 2.67 M solution contains CrO$_3$ (26.7 g) and concentrated H$_2$SO$_4$ (23 ml) made up to 100 ml with water. Temperatures are in °C. The following abbreviations are used:

TLC—thin layer chromatography using SiO$_2$; PE—petroleum ether (boiling at 40°–60° unless otherwise stated);

DIBAL—diisobutylaluminium hydride; THF—tetrahydrofuran;

DMF—dimethylformamide; ER—ether; EA—ethyl acetate;

DMSO—dimethylsulphoxide. Chromatography was carried out using silica gel unless otherwise stated. 'Dried' refers to drying with MgSO$_4$. 'Hyflo' is a filtration aid.

Intermediate 1

(endo,anti)-(±)-5-Hydroxy-7-(4-morpholinyl)bicyclo[2.2.1]heptan-2-one

A mixture of (endo,anti)-5-acetyl-7-(4-morpholinyl)-bicyclo[2.2.1]heptan-2-one (164 g) and 5 N NaOH solution (750 ml) was stirred for 3 h and then extracted with CH$_2$Cl$_2$ (4×500 ml). The dried organic layers were evaporated in vacuo to give a semi-solid. Trituration with ER (500 ml) gave the *title compound* (83 g) as prisms, m.p. 119°–121°.

Intermediate 2

(a) (endo,anti)-(±)-5-[[(1,1'-Biphenyl-4-yl]methoxy]-7-(4-morpholinyl)bicyclo[2.2.1]heptan-2-one To a solution of Intermediate 1 (10.5 g), 1-(bromomethyl)-1,1'-biphenyl (13.6 g) and benzyltriethyl ammonium chloride (1.14 g) in CH$_2$Cl$_2$ (200 ml) was added 17 N NaOH (100 ml) and the mixture stirred vigorously for 18 h. The layers were separated and the aqueous layer extracted with CH$_2$Cl$_2$ (3×100 ml). The combined organic layers were washed with water (200 ml), dried and evaporated in vacuo. The residue was crystallised from iso-propyl acetate to give the title compound (15 g) as prisms, m.p. 149.5°–151.5°.

The following compounds were prepared by a similar procedure.

(b) (endo,anti)-(±)-5-[4-Methoxy(phenylmethoxy)]-7-(4-morpholinyl)bicyclo[2.2.1]heptan-2-one, m.p. 109°–111°, from Intermediate 1 and p-methoxybenzyl bromide. Purification by chromatography using 3:1 ER-PE through to 5:1 ER-methanol as eluent.

(c) (±)-4-[(endo,endo,anti)-2-[[(1,1'-Biphenyl)-4-yl]methoxy]-5-[(tetrahydro-2H-pyran-2-yl)oxy]bicyclo-[2.2.1]heptan-7-yl]morpholine, m.p. 109°–110° from Intermediate 27. Purification by chromatography using 7:3 ER-PE as eluent.

(d) (endo,anti)-(±)-5-[[(1,1'-Biphenyl)-4-yl]methoxy]-7-(1-piperidinyl)bicyclo[2.2.1]heptan-2-one, m.p. 89°–91° from Intermediate 57. Purification by chromatography using 3:2 PE-ER as eluent.

Intermediate 3

(a) (endo,anti)-(±)-6-[[(1,1'Biphenyl)-4-yl]methoxy]-8-(4-morpholinyl)-2- oxabicyclo[3.2.1]octan-3-one 38% Peracetic acid in acetic acid (20 ml) was added dropwise over 10 min. to a stirred solution of Intermediate 2a (12.5 g) in $CH_2Cl_2$ (60 ml) maintained at 12°–15°. Stirring was continued at 15°–20° for 24 h, the mixture then cooled to 5° and treated with a solution of $Na_2SO_3$ (25.1 g) in water (125 ml) whilst maintaining the temperature below 20°. Isopropyl acetate (90 ml) was added and the aqueous phase was separated. The organic phase was extracted with 1 N NaOH (60 ml) and water (2×60 ml), then dried and reduced in volume to about 35 ml. On cooling to 20° the title compound crystallised and was collected and dried (6.25 g), m.p. 137°–139°.

The following compounds were prepared by a similar procedure:

(b) (endo,anti)-(±)-6-[4-Methoxy(phenylmethoxy)]-8-(4-morpholinyl)-2-oxabicyclo[3.2.1]octan-3-one, m.p. 158°–160°, from Intermediate 2b. Purification from $CH_2Cl_2$-PE.

(c) (endo,anti)-(±)-6-[[(1,1'-Biphenyl)-4-yl]methoxy]-8-(1-piperidinyl)-2-oxabicyclo[3.2.1]octan-3-one, m.p. 88°–90° from Intermediate 2d.

(d) (endo,anti)-(±)-6-Decyloxy-8-(4-morpholinyl)-2-oxabicyclo[3.2.1]octan-3-one m.p. 59°–61°, from intermediate 80. Purification from PE.

Intermediate 4

(a) (1α,2β,3α,5α)-(±)-5-[[(1,1'-Biphenyl)-4-yl]methoxy]-3-hydroxy-2-(4-morpholinyl)cyclopentane acetaldehyde DIBAL in hexane (1.4 M; 6.9 ml) was added dropwise to a solution of Intermediate 3a (1.9 g) in dry $CH_2Cl_2$ (30 ml) under nitrogen at −70°. Stirring was continued for 2 h at −70° when methanol (50 ml) was cautiously added and the mixture then allowed to come to ambient temperature and stirred for a further 3 h. The mixture was filtered through hyflo and the filtrate evaporated in vacuo. The residue was taken up into $CH_2Cl_2$ (50 ml), dried, filtered and concentrated to give the title compound as a glass (1.8 g) I.R. ($CHBr_3$) 3580, 1718 $cm^{-1}$.

The following compounds were prepared by a similar procedure:

(b) (1α,2β,3α,5α)-(±)-3-Hydroxy-5-[4-methoxy(phenylmethoxy)]-2-(4-morpholinyl)cyclopentane acetaldehyde, from Intermediate 3b. Purification by chromatography using 98:2 $CHCl_3$-methanol as eluent. TLC 95:5 $CHCl_3$-methanol Rf 0.8.

(c) (1α,2α,3α,5α)-(±)-5-[[(1,1'-Biphenyl)-4-yl]methoxy]-3-hydroxy-2-(4-morpholinyl)cyclopentane acetaldehyde, m.p. 136°–138° from Intermediate 30.

(d) (3aα,4α,5β,6aα)-(±)-Hexahydro-5-[(tetrahydro-2H-pyran-2-yl)oxy]-4-(4-thiomorpholinyl)-2H-cyclopenta(b)furan-2-ol, from Intermediate 55a. TLC 9:1 Benzene-methanol Rf 0.25

(e) (1α,2β,3α,5α)-(±)-5-[[(1,1'-Biphenyl)-4-yl]methoxy]-3-hydroxy-2-(1-piperidinyl)cyclopentane acetaldehyde, from Intermediate 3c. TLC 85:15 ER-methanol Rf 0.38.

(f) (3aα,4α,5β,6aα)-(±)-Hexahydro-4-(hexahydro-1,4-oxazepin-4-yl)-5-[(tetrahydro-2H-pyran-2-yl)oxy]-2H-cyclopenta(b) furan-2-ol, from Intermediate 55b. TLC 9:1 ER-methanol Rf 0.31.

(g) (1α,2β,3α,5α)-(±)-5-Decyloxy-3-hydroxy-2-(4-morpholinyl)cyclopentane acetaldehyde from Intermediate 3d. TLC ($SiO_2$) EA $R_f$ 0.21.

Intermediate 5

(a) (1α,2β,3α,4α)-(±)-4-[[(1,1'-Biphenyl)-4-yl]methoxy]-3-(3-methoxy-2-propenyl)-2-(4-morpholinyl)-cyclopentanol To a cold (0°) stirred solution of potassium tert-butoxide (1.55 g) in dry THF (40 ml) under nitrogen, was added portionwise (methoxymethyl)triphenyl phosphonium chloride (4.72 g). The resulting suspension was stirred for 25 min. whereupon a solution of Intermediate 4a (1.82 g) in dry THF (15 ml) was added dropwise. Stirring was continued at room temperature for 1.5 h. The reaction mixture was poured into brine, the pH adjusted to 6.5, and the mixture extracted with EA. The dried extracts were evaporated to leave a viscous oil. This crude material was flash chromatographed on silica. Eluting with 95:5 EA-methanol and recycling of the impure fractions gave the title compound as an oil (1.29 g). IR ($CHBr_3$) 3950(br), 3540, 1668 $cm^{-1}$.

The following compounds were prepared in a similar manner.

(b) (1α,2α,3β,4α)-(±)-2-(3-Methoxy-2-propenyl)-4-[(tetrahydro-2H-pyran-2-yl)oxy]-3-(4-thiomorpholinyl)cyclopentanol, from Intermediate 4d. Purification by chromatography using ether as eluent. TLC ER Rf 0.28.

(c) (1α,2α,3β,4α)-(±)-2-(3-Methoxy-2-propenyl)-3-(1-piperidinyl)-4-[(tetrahydro-2H-pyran-2-yl)oxy]cyclopentanol, from (3aα,4α,5β,6aα)-(±)-hexahydro-4-(1-piperidinyl)-5-[(tetrahydro-2H-pyran-2-yl)oxy]-2H-cyclopenta(b)furan-2-ol. TLC 4:1 EA-methanol Rf 0.22.

Intermediate 6

(1α,2β,3α,5α)-(±)-5-[[(1,1'-Biphenyl)-4-yl]methoxy]-3-hydroxy-2-(4-morpholinyl)-cyclopentane propanal, hydrochloride Intermediate 5a (1.835 g) was dissolved in 1:1 acetone/0.5 N $H_2SO_4$ (65 ml) and was left standing overnight at room temperature. The acetone was evaporated and the residue treated with 8% $NaHCO_3$ solution and extracted with EA. The dried extracts were evaporated to give a foam (1.73 g) which was dissolved in ether and treated with ethereal hydrogen chloride. The title compound was filtered off and dried, m.p. 169°–172°.

Intermediate 7

(a) (1α,2α,3β,4α)-(±)-2-(3-Methoxy-2-propenyl)-3-(4-morpholinyl)-4-[(tetrahydro-2H-pyran-2-yl)oxy]cyclopentanol, acetate (ester)

To a cold (0°) stirred solution of potassium tert-butoxide (2.15 g) in dry THF (40 ml) under nitrogen, was added portionwise (methoxymethyl)triphenyl phosphonium chloride (6.57 g). The suspension was stirred for 15 min., whereupon a solution of (3aα,4α,5β,6aα)-hexahydro-4-(4-morpholinyl)-5-(tetrahydro-2H-pyran-2-yl)oxy-2H-cyclopenta(b)-furan-2-ol (2 g) in dry THF (30 ml) was added dropwise. Stirring was continued at room temperature for 1 h, when methanol (30 ml) was added followed by evaporation of the mixture to dryness. The residue was treated with acetic anhydride (8 ml) and pyridine (10 ml) and left for 40 h. Evaporation in vacuo gave a residue which was treated with 8% NaHCO$_3$ solution (50 ml) and extracted with CH$_2$Cl$_2$ (3×20 ml). The combined extracts were washed with brine (2×15 ml), dried and concentrated. Purification of the residue, initially by chromatography using 4:1 ER-methanol as eluent, and then by trituration with PE gave the title compound as an oil (13.23 g). IR (Neat) 1735, 1655 cm$^{-1}$.

The following compounds were prepared in a similar manner:

(b) (1α,2α,3β,4α)-(±)-2-(3-Methoxy-2-propenyl)-4-[(tetrahydro-2H-pyran-2-yl)oxy]-3-(4-thiomorpholinyl)cyclopentanol, acetate (ester), S-dioxide, m.p. 131°-134° from Intermediate 63. Purification initially by chromatography using 1:1 EA-PE as eluent, followed by crystallisation from isopropanol-ER-isopentane.

(c) (1α,2α,3β,4α)-(±)-3-(Hexahydro-1,4-oxazepin-4-yl)-2-(3-methoxy-2-propenyl)-4-[(tetrahydro-2H-pyran-2-yl)oxy]cyclopentanol, acetate (ester), from Intermediate 4f. Purification by chromatography using 95:5 ER-methanol as eluent. TLC 19:1 ER-methanol Rf 0.65.

Intermediate 8

(1α,2α,3β,4α)-(±)-2-(3-Methoxy-2-propenyl)-3-(4-morpholinyl))-4-[(tetrahydro-2H-pyran-2-yl)oxy]cyclopentanol A solution of Intermediate 7a (0.3 g) in 0.5 N NaOH (10 ml) was left to stand for 10 min., then extracted with ER (3×20 ml). The combined extracts were dried, filtered and evaporated to given the title compound as an oil (0.25 g). IR (Neat) 3450, 1655 cm$^{-1}$.

Intermediate 9

(a) (1α,2β,3β,5β)-(±)-4-[3-(2-Naphthalenylmethoxy)-2-(3-methoxy-2-propenyl)-5-[(tetrahydro-2H-pyran-2-yl)oxy]cyclopentyl]morpholine NaH (0.48 g, 80% dispersion in oil) was added to a solution of Intermediate 8 (2.2 g) and 2-(bromomethyl)naphthalene (3.56 g) in dry DMF (8 ml) at 0°. After stirring for 7 h, the suspension was poured into saturated NH$_4$Cl solution (75 ml) and extracted into ER (3×50 ml). The combined extracts were dried and concentrated, and the residue chromatographed on silica using ER as eluent to give the title compound as an oil (2.1 g). IR (Neat) 1716, 1655 cm$^{-1}$.

The following compounds were prepared by a similar procedure:

(b) (1α,2β,3β,5β)-(±)-4-[2-(3-Methoxy-2-propenyl)-3-[4-(1,1-dimethylethyl)phenylmethoxy]-5-[(tetrahydro-2H-pyran-2-yl)oxy]cyclopentyl]morpholine, from Intermediate 8 and 4-(1,1-dimethylethyl)phenylmethyl bromide. Purification by chromatography using ER as eluent. IR (Neat) 1650, 1120 cm$^{-1}$.

(c) (1α,2β,3β,5β)-(±)-4-[3-(4-Cyclohexylphenylmethoxy)-2-(3-methoxy-2-propenyl)-5-[(tetrahydro-2H-pyran-2-yl)oxy]cyclopentyl]morpholine, from Intermediate 8 and 4-cyclohexylphenylmethyl iodide. Purification by chromatography using ER as eluent.

(d) (1α,2β,3β,5β)-(±)-4-[2-(3-Methoxy-2-propenyl)-3-(pentyloxy)-5-[(tetrahydro-2H-pyran-2-yl)oxy]cyclopentyl]morpholine, from Intermediate 8 and n-pentyl-tosylate. Purification by chromatography using EA as eluent.

(e) (1α,2β,3β,5β)-(±)-4-[2-(3-Methoxy-2-propenyl)-3-[4-(phenylmethyl)phenylmethoxy]-5-[(tetrahydro-2H-pyran-2-yl)oxy]cyclopentyl]morpholine, from Intermediate 8 and 1-(bromomethyl)-4-(phenylmethyl)benzene. Purification by chromatography using ER as eluent.

(f) (1α,2β,3β,5β)-(±)-4-[3-[[4'-Chloro(1,1'-biphenyl)-4-yl]methoxy]-2-(3-methoxy-2-propenyl)-5-[(tetrahydro-2H-pyran-2-yl)oxy]cyclopentyl]morpholine, from Intermediates 8 and 68. IR (Neat) 1650, 1120 cm$^{-1}$.

(g) (1α,2β,3β,5β)-(±)-4-[2-(3-Methoxy-2-propenyl)-3-(2-propenyloxy)-5-[(tetrahydro-2H-pyran-2-yl)oxy]cyclopentyl]morpholine, from Intermediate 8 and allyl bromide.

(h) (1α,2β,3β,5β)-(±)-4-[2-(3-Methoxy-2-propenyl)-3-[4-methylthio(phenylmethoxy)]-5-[(tetrahydro-2H-pyran-2-yl)oxy]cyclopentyl]morpholine, from Intermediate 8 and 1-(bromomethyl)-4-(methylthio)benzene. Purification by chromatography using ER as eluent. IR (Neat) 1650, 1120 cm$^{-1}$.

(i) (1α,2β,3β,5β)-(±)-4-[2-(3-Methoxy-2-propenyl)-5-[(tetrahydro-2H-pyran-2-yl)oxy]-3-[(4-thien-2-2-yl)phenylmethoxy]cyclopentyl]morpholine, from Intermediates 8 and 24a. Purification by chromatography using ER as eluent.

(j) (1α,2β,3β,5β)-(±)-4-[2-(3-Methoxy-2-propenyl)-3-[[(1,1':4',1''-terphenyl)-4-yl]methoxy]-5-[(tetrahydro-2H-pyran-2-yl)oxy]cyclopentyl]morpholine, from Intermediates 8 and 24b. Purification by chromatography using ER as eluent. TLC ER Rf 0.18.

(l) [1α,2β,3β(E),5β]-(±)-4-[2-(3-Methoxy-2-propenyl)-3-[(3-phenyl-2-propenyl)oxy]-5-[(tetrahydro-2H-pyran-2-yl)oxy]cyclopentyl]morpholine, from Intermediate 8 and cinnamyl bromide. Purification by chromatography using ether as eluent.

(m) (1α,2β,3β,5β)-(±)-4-[3-[[(1,1'-Biphenyl)-4-yl]methoxy]-2-(3-methoxy-2-propenyl)-5-[(tetrahydro-2H-pyran-2-yl)oxy]cyclopentyl]thiomorpholine, from Intermediate 5b and 1-(bromomethyl)-1,1'-biphenyl. Purification by chromatography using 3:2 ER-PE. TLC ER Rf 0.42.

(n) 1α,2β,3β,5β)-(±)-4-[3-[[4'-Methoxy(1,1'-biphenyl)-4-yl]methoxy]-2-(3-methoxy-2-propenyl)-5-[(tetrahydro-2H-pyran-2-yl)oxy]cyclopentyl]thiomorpholine, S-dioxide, from Intermediate 59a and 4-(bromomethyl)-4'-methoxy(1,1'-biphenyl). Purification by chromatography using CH$_2$Cl$_2$ followed by ER as eluents. TLC ER Rf 0.41.

(o) (1α,2β,3β,5β)-(±)-4-[2-(3-Methoxy-2-propenyl)-3-[[4'-methyl(1,1'-biphenyl)-4-yl]methoxy]-5-(tetrahydro-2H-pyran-2-yl)oxy]cyclopentyl]thiomorpholine, S-dioxide, from Intermediates 59a and 66. Purification by chromatography using CH$_2$Cl$_2$ followed by 4:1 ER-PE as eluent.

(p) (1α,2β,3β,5β)-(±)-4-[2-(3-Methoxy-2-propenyl)-3-[4-(phenylmethyl)phenylmethoxy]-5-[(tetrahydro-2H-pyran-2-yl)oxy]cyclopentyl]thiomorpholine, S-dioxide, from Intermediate 59a and 1-(bromomethyl)-4-(phenylmethyl)benzene. Purification by chromatography using CH$_2$Cl$_2$ followed by ER as eluents. TLC EA Rf 0.5.

(q) (1α,2β,3β,5β)-(±)-4-[3-[[(1,1'-Biphenyl)-4-yl]methoxy]-2-(3-methoxy-2-propenyl)-5-[(tetrahydro-2H-pyran-2-yl)oxy]cyclopentyl]thiomorpholine, S-dioxide, from Intermediate 59a and 1-(bromomethyl)-1,1'-biphenyl. TLC 95:5 ER-methanol Rf 0.7.

(r) (1α,2β,3β,5β)-(±)-4-[3-[(1,1'-Biphenyl)-4-yl]methoxy]-2-(3-methoxy-2-propenyl)-5-[(tetrahydro-2H-pyran-2-yl)oxy]cyclopentyl]hexahydro-1,4-oxazepin, from Intermediate 59b. TLC 97:3 ER-methanol Rf 0.68.

(s) (1α,2β,3β,5β)-(±)-1-[3-[[4'-Methoxy(1,1'-biphenyl)-4-yl]methoxy]-2-(3-methoxy-2-propenyl)-5-[(tetrahydro-2H-pyran-2-yl)oxy]cyclopentyl]piperidine, from Intermediate 5c. Purification by chromatography using 98:2 $CH_2Cl_2$-methanol as eluent.

(t) (1α,2β,3β,5β)-(±)-4-[3-[[(1,1'-Biphenyl)-4-yl]propoxy]-2-(3-methoxy-2-propenyl)-5-[(tetrahydro-2H-pyran-2-yl)oxy]cyclopentyl]morpholine, from Intermediates 8 and 60. Purification by chromatography using EA as eluent.

(u) (1α,2β,3β,5β)-(±)-4-[3-[[3'-Methoxy(1,1'-biphenyl)-4-yl]methoxy]-2-(3-methoxy-2-propenyl)-5-[(tetrahydro-2H-pyran-2-yl)oxy]cyclopentyl]morpholine, from Intermediates 8 and 24c. Purification by chromatography using EA as eluent.

(v) (1α,2β,3β,5β)-(±)-4-[3-[[4'-Methoxy(1,1'-biphenyl)-3-yl]methoxy]-2-(3-methoxy-2-propenyl)-5-[(tetrahydro-2H-pyran-2-yl)oxy]cyclopentyl]morpholine, from Intermediate 8 and 3-(bromomethyl)-4'-methoxy(1,1'-biphenyl). Purification by chromatography using EA as eluent.

Intermediate 10

(a) (1α,2β,3α,5α)-(±)-3-Hydroxy-2-(4-morpholinyl)-5-(2-naphthalenylmethoxy)cyclopentanepropanal A solution of Intermediate 9a (2.1 g) in acetone (10 ml) containing 2 N hydrochloric acid (5 ml) was allowed to stand at room temperature for 1 h. After evaporation in vacuo the residue was neutralised with 8% $NaHCO_3$ solution and extracted with $CH_2Cl_2$ (3×30 ml). The combined extracts were dried, filtered and concentrated to afford the title compound as a viscous oil (1.7 g). IR (Neat) 3420, 1720 cm$^{-1}$ The following compounds were prepared by a similar procedure:

(b) (1α,2β,3α,5α)-(±)-3-Hydroxy-5-[4-(1,1-dimethylethyl)-phenylmethoxy]-2-(4-morpholinyl)cyclopentanepropanal, from Intermediate 9b. TLC 4:1 ER-methanol Rf 0.52.

(c) (1α,2β,3α,5α)-(±)-5-(4-Cyclohexylphenylmethoxy)-3-hydroxy-2-(4-morpholinyl)cyclopentanepropanal, from Intermediate 9c. TLC 17:3 ER-methanol Rf 0.28.

(d) (1α,2β,3α,5α)-(±)-3-Hydroxy-2-(4-morpholinyl)-5-(pentyloxy)cyclopentanepropanal, from Intermediate 9d. TLC 95:5 EA-methanol Rf 0.08.

(e) (1α,2β,3α,5α)-(±)-3-Hydroxy-2-(4-morpholinyl)-5-[4-(phenylmethyl)phenylmethoxy]cyclopentanepropanal, from Intermediate 9e. Purification by chromatography using 9:1 ER-methanol as eluent.

(f) (1α,2β,3α,5α)-(±)-5-[[4'-Chloro(1,1'-biphenyl)-4-yl]methoxy]-3-hydroxy-2-(4-morpholinyl)cyclopentanepropanal, from Intermediate 9f. Purification by chromatography using $CHCl_3$ through to 98:2 $CHCl_3$-methanol as eluent.

(g) (1α,2β,3α,5α)-(±)-3-Hydroxy-2-(4-morpholinyl)-5-(2-propenyloxy)cyclopentanepropanal, from Intermediate 9g. Purification by chromatography using 4:1 ER-methanol as eluent.

(h) (1α,2β,3α,5α)-(±)-3-Hydroxy-5-[4-methylthio(phenylmethoxy)]-2-(4-morpholinyl)cyclopentanepropanal, from Intermediate 9h. Purification by chromatography using 85:15 ER-methanol as eluent. TLC 85:15 ER-methanol Rf 0.28.

(i) (1α,2β,3α,5α)-(±)-3-Hydroxy-2-(4-morpholinyl)-5-[(4-thien-2-yl)phenylmethoxy]cyclopentanepropanal, from Intermediate 9i. Purification by chromatography using $CHCl_3$ through to 98:2 $CHCl_3$-methanol as eluent. TLC 95:5 $CHCl_3$-methanol Rf 0.3.

(j) (1α,2β,3α,5α)-(±)-3-Hydroxy-2-(4-morpholinyl)-4-[[(1,1':4',1''-terphenyl)-4-yl]methoxy]cyclopentanepropanal, m.p. 151°-153° from Intermediate 9j.

(l) [1α,2β,3α,5α(E)]-(±)-3-Hydroxy-2-(4-morpholinyl)-5-[(3-phenyl-2-propenyl)oxy]cyclopentanepropanal, from Intermediate 9l. IR (CHBr$_3$) 3580, 3560, 1720 cm$^{-1}$ (m) (1α,2β,3α,5α)-(±)-5-[[(1,1'-Biphenyl)-4-yl]methoxy]-3-hydroxy-2-(4-thiomorpholinyl)cyclopentanepropanal, m.p. 109°-110° from Intermediate 9m. Purification by chromatography using ER as eluent.

(n) (1α,2β,3α,5α)-(±)-3-Hydroxy-5-[[4'-methoxy(1,1'-biphenyl)-4-yl]methoxy]-2-(4-thiomorpholinyl)cyclopentanepropanal, S-dioxide, from Intermediate 9n. IR (CHBr$_3$) 3580, 2720, 1720 cm$^{-1}$ (o) (1α,2β,3α,5α)-(±)-3-Hydroxy-5-[[4'-methyl(1,1'-biphenyl)-4-yl]methoxy]-2-(4-thiomorpholinyl)cyclopentanepropanal, S-dioxide, from Intermediate 9o. IR (CHBr$_3$) 3580, 2725, 1720 cm$^{-1}$ (p) (1α,2β,3α,5α)-(±)-3-Hydroxy-5-[4-(phenylmethyl)phenylmethoxy]-2-(4-thiomorpholinyl)cyclopentanepropanal, S-dioxide, from Intermediate 9p. IR (CHBr$_3$) 3580, 2720, 1720 cm$^{-1}$ (q) (1α,2β,3α,5α)-(±)-5-[[(1,1'-Biphenyl)-4-yl]methoxy]-3-hydroxy-2-(4-thiomorpholinyl)cyclopentanepropanal, S-dioxide, m.p. 152.5°-154° (dec.) from Intermediate 9q.

(r) (1α,2β,3α,5α)-(±)-5-[[1,1'-Biphenyl)-4-yl]methoxy]-2-(hexahydro-1,4-oxazepin-4-yl)-3-hydroxycyclopentanepropanal, from Intermediate 9r. IR (CHBr$_3$) 3580, 2730, 1720 cm$^{-1}$.

(s) (1α,2β,3α,5α)-(±)-3-Hydroxy-5-[[4'-methoxy(1,1'-biphenyl)-4-yl]methoxy]-2-(1-piperidinyl)cyclopentanepropanal, from Intermediate 9s. IR (CHBr$_3$) 3520, 2730, 1720 cm$^{-1}$ (t) (1α,2β,3α,5α)-(±)-5-[3-[1,1'-Biphenyl)-4-yl]propoxy]-3-hydroxy-2-(4-morpholinyl)cyclopentanepropanal, from Intermediate 9t. IR (CHBr$_3$) 3580, 2730, 1723 cm$^{-1}$ (u) (1α,2β,3α,5α)-(±)-[3-Hydroxy-5-[[3'-methoxy(1,1'-biphenyl)-4-yl]methoxy]-2-(4-morpholinyl)]cyclopentanepropanal, from Intermediate 9u. IR (CHBr$_3$) 3580, 2720, 1720 cm$^{-1}$ (v) (1α,2β,3α,5α)-(±)-[3-Hydroxy-5-[[4'-methoxy(1,1'-biphenyl)-3-yl]methoxy]-2-(4-morpholinyl)]cyclopentanepropanal, from Intermediate 9v. IR (CHBr$_3$) 3560, 2720, 1720 cm$^{-1}$ Intermediate 11

(1α,2β,3α,5α)-(±)-3-Hydroxy-5-[4-methoxy(phenylmethoxy)]-2-(4-morpholinyl)cyclopentanepropanal Prepared as an oil from Intermediate 4b according to the methods described for Intermediates 5 and 6. IR (Neat) 3380(br.), 2720, 1720, 1118 cm$^{-1}$ Intermediate 12

(a) [1α(Z),2β,3α,5α]-(±)-7-[5-[(1,1'-Biphenyl)-4-yl]methoxy]-3-hydroxy-2-(4-morpholinyl)cyclopentyl]-4-heptenoic acid To an intimate mixture of potassium tert-butoxide (1.29 g) and (3-carboxypropyl)triphenylphosphonium bromide (2.41 g) under nitrogen was added dry THF (50 ml). The suspension formed was stirred for 30 min whereupon a solution of the free base of Intermediate 6 (1.18 g) in dry THF (50 ml) was added dropwise. Stirring was maintained for 1.5 h whereupon water was added and all organic solvents were evaporated. The pH of the remaining suspension was adjusted to 10 with 2 N NaOH solution and the suspension was then extracted with EA to remove phosphorus contaminants. The pH was then adjusted to about 6.5 with phosphate buffer and the product extracted from the suspension with EA. The dried extracts were filtered and concentrated to give the title compound as a foam (0.93 g). IR (CHBr$_3$) 3460, 1710 cm$^{-1}$

Hydrochloride salt

To a solution of Intermediate 12a (0.25 g) in EA (5 ml) was added ethereal hydrogen chloride until no more cloudiness was produced. The solvents were decanted and the resulting oil repeatedly washed with dry ER to give a powder (0.13 g), m.p. 125.5°–126.5°.

Methanesulphonate salt

To a solution of Intermediate 12a (0.044 g) in EA (2 ml) was added methanesulphonic acid (0.01 g) at 20° and the mixture stirred for 1 h. The solid was filtered off, washed with EA and dried. Recrystallisation from ethanol gave material of m.p. 171°–174°. The following compounds were prepared by a similar procedure:

(b) [1α(Z),2β,3α,5α]-(±)-7-[3-Hydroxy-2-(4-morpholinyl)-5-(2-naphthalenylmethoxy)cyclopentyl]-4-heptenoic acid, from Intermediate 10a. Purification by chromatography using 85:15 ER-methanol as eluent. IR (Neat) 3450–2300(br.), 1715 cm$^{-1}$ (c) [1α(Z),2β,3α,5α]-(±)-7-[3-Hydroxy-5-[4-methoxy(phenylmethoxy)]-2-(4-morpholinyl)cyclopentyl]-4-heptenoic acid, from Intermediate 11. Purification by chromatography using 95:5 CHCl$_3$-methanol as eluent. IR (CHBr$_3$) 3580, 3500, 1720, 1710 cm$^{-1}$ (d) [1α(Z),2β,3α,5α]-(±)-7-[3-Hydroxy-5-[4-(1,1-dimethylethyl)phenylmethoxy]-2-(4-morpholinyl)-cyclopentyl]-4-heptenoic acid, from Intermediate 10b. Purification by chromatography using 9:1 ER-methanol as eluent. IR (CHBr$_3$) 3500, 1740, 1710 cm$^{-1}$ (e) [1α(Z),2β,3α,5α]-(±)-7-[5-(4-Cyclohexylphenylmethoxy)-3-hydroxy-2-(4-morpholinyl)cyclopentyl]-4-heptenoic acid, from Intermediate 10c. IR (CHBr$_3$) 3500, 1720, 1708 cm$^{-1}$ (f) [1α(Z),2β,3α,5α]-(±)-7-[3-Hydroxy-2-(4-morpholinyl)-5-(pentyloxy)cyclopentyl]-4-heptenoic acid, from Intermediate 10d. Purification by chromatography using acetone as eluent.

(g) [1α(Z),2β,3α,5α]-(±)-7-[3-Hydroxy-2-(4-morpholinyl)-5-[4-(phenylmethyl)phenylmethoxy]cyclopentyl]-4-heptenoic acid, from Intermediate 10e. Purification by chromatography using 4:1 ER-methanol as eluent.

(h) [1α(Z),2β,3α,5α]-(±)-7-[5-[[4'-Chloro(1,1'-biphenyl)-4-yl]methoxy]-3-hydroxy-2-(4-morpholinyl)-cyclopentyl]-4-heptenoic acid, from Intermediate 10f. Purification by chromatography using CHCl$_3$ through to 96:4 CHCl$_3$-methanol as eluent. IR (CHBr$_3$) 3500, 1710 cm$^{-1}$ (i) [1α(Z),2β,3α,5α]-(±)-7-[3-Hydroxy-2-(4-morpholinyl)-5-(2-propenyloxy)cyclopentyl]-4-heptenoic acid, from Intermediate 10g. Purification by chromatography using 9:1 ER-methanol as eluent. IR (CHBr$_3$) 3500, 1740–1710(br.) cm$^{-1}$ (j) [1α(Z),2β,3α,5α]-(±)-7-[3-Hydroxy-5-[4-methylthio(phenylmethoxy)]-2-(4-morpholinyl)cyclopentyl]-4-heptenoic acid, from Intermediate 10h. Purification by chromatography using 9:1 ER-methanol as eluent. IR (CHBr$_3$) 3600–3400(br.), 1730(sh.), 1710 cm$^{-1}$ (k) [1α(Z),2β,3α,5α]-(±)-7-[3-Hydroxy-2-(4-morpholinyl)-5-[(4-thien-2-yl)phenylmethoxy]cyclopentyl]-4-heptenoic acid, from Intermediate 10i. Purification by chromatography using CHCl$_3$ through to 94:6 CHCl$_3$-methanol as eluent. IR (CHBr$_3$) 3500, 1738, 1710 cm$^{-1}$ (l) [1α(Z),2β,3α,5α]-(±)-7-[3-Hydroxy-2-(4-morpholinyl)-5-[[(1,1':4,1''-terphenyl)-4-yl]methoxy]cyclopentyl]-4-heptenoic acid, from Intermediate 10j. IR (CHBr$_3$) 3500, 1720 cm$^{-1}$ (m) [1α(Z),2β,3α,5α]-(±)-9-[5-[[(1,1'-Biphenyl)-4-yl]methoxy]-3-hydroxy-2-(4-morpholinyl)cyclopentyl]-6-nonenoic acid, from Intermediate 6 and (5-carboxypentyl)triphenylphosphonium bromide. IR (CHBr$_3$), 3510, 1730 (Sh.), 1710 cm$^{-1}$ (o) [1α(Z),2β,3α,5α(E)]-(±)-7-[3-Hydroxy-2-(4-morpholinyl)-5-[(3-phenyl-2-propenyl)oxy]cyclopentyl]-4-heptenoic acid, from Intermediate 10l. Purification by chromatography using 9:1 ether-methanol as eluent. IR (CHBr$_3$) 3500, 1720 cm$^{-1}$ (p) [1α(Z),2β,3α,5α]-(±)-7-[5-[[1,1'-Biphenyl)-4-yl]methoxy]-3-hydroxy-2-(4-thiomorpholinyl)cyclopentyl-4-heptenoic acid, from Intermediate 10m. IR (CHBr$_3$) 3500, 1730, 1710 cm$^{-1}$ (q) [1α(Z),2β,3α,5α]-(±)-7-[3-Hydroxy-5-[[4'-methoxy(1,1'-biphenyl)-4-yl]methoxy]-2-(4-thiomorpholinyl)cyclopentyl]-4-heptenoic acid, S-dioxide, m.p. 113°–115° from Intermediate 10n. Purification by chromatography using 98:2 through to 96:4 ER-methanol as eluent.

(r) [1α(Z),2β,3α,5α]-(±)-7-[3-Hydroxy-5-[[4'-methyl(1,1'-biphenyl)-4-yl]methoxy]-2-(4-thiomorpholinyl)-cyclopentyl]-4-heptenoic acid, S-dioxide, m.p. 119.5°–121.5° from Intermediate 10o.

(s) [1α(Z),2β,3α,5α]-(±)-7-[3-Hydroxy-5-[4-(phenylmethyl)phenylmethoxy]-2-(4-thiomorpholinyl)cyclopentyl]-4-heptenoic acid, S-dioxide, m.p. 127.5°–128.5° from Intermediate 10p. Purification by chromatography using 96:4 ER-methanol as eluent.

(t) [1α(Z),2β,3α,5α]-(±)-7-[5-[[(1,1'-Biphenyl)-4-yl]methoxy]-3-hydroxy-2-(4-thiomorpholinyl)cyclopentyl]-4-heptenoic acid, S-dioxide, m.p. 109.5°–111.5° from Intermediate 10q. Purification by chromatography using 98:2 ER-methanol as eluent.

(u) [1α(Z),2β,3α,5α]-(±)-7-[5-[[(1,1'-Biphenyl)-4-yl]methoxy]-2-(hexahydro-1,4-oxazepin-4-yl)-3-hydroxycyclopentyl]-4-heptenoic acid, from Intermediate 10r. TLC (SiO$_2$) 3:1 ER-methanol Rf 0.29.

(v) [1α(Z),2β,3α,5α]-(±)-7-[3-Hydroxy-5-[[4'-methoxy-(1,1'-biphenyl)-4-yl]-methoxy]-2-(1-piperidinyl)cyclopentyl]-4-heptenoic acid, compound with piperazine (2:1), m.p. 106°–112° from Intermediate 10s. The title compound crystallised from a solution of the acid and piperazine in 2:1 EA-ER.

(w) [1α(Z),2β,3α,5α]-(±)-7-[5-[3-[(1,1'-Biphenyl)-4-yl]propoxy]-3-hydroxy-2-(4-morpholinyl)cyclopentyl]-4-heptenoic acid, from Intermediate 10t. Purification by chromatography using 5:1 EA-methanol as eluent. TLC 5:1 EA-methanol Rf 0.3.

(x) [1α(Z),2β,3α,5α]-(±)-7-[3-Hydroxy-5-[[3'-methoxy-(1,1'-biphenyl)-4-yl]-methoxy]-2-(4-morpholinyl)cyclopentyl]-4-heptenoic acid, from Intermediate 10u. IR (CHBr$_3$) 3500, 1725(sh.), 1710 cm$^{-1}$.

(y) [1α(Z),2β,3α,5α]-(±)-7-[3-Hydroxy-5-[[4'-methoxy(1,1'-biphenyl)-3-yl]-methoxy]-2-(4-morpholinyl)cyclopentyl]-4-heptenoic acid, from Intermediate 10v. IR (CHBr$_3$) 3500, 1735 (sh.), 1710 cm$^{-1}$.

(z) [1α(Z),2β,3α,5α]-(±)-7-[5-Decyloxy-3-hydroxy-2-(4-morpholinyl)cyclopentyl]-4-heptenoic acid, from Intermediate 17d. IR (CHBr$_3$) 3500, 1725 (sh), 1710 cm$^{-1}$.

Intermediate 13

[1α(Z),2β,3α,5α]-(±)-8-[5-[[(1,1'-Biphenyl)-4-yl]methoxy]-3-hydroxy-2-(4-morpholinyl)cyclopentyl]-5-octenoic acid Prepared from Intermediate 6 (1 g) and (4-carboxybutyl)triphenylphosphonium bromide (3.17 g) in an analogous manner to that described for Intermediate 12a. The title compound was isolated as a foam (0.92 g). IR (CHBr$_3$) 3500, 1740, 1705 cm$^{-1}$.

Intermediate 14

[1α(Z),2β,3α,5α]-(±)-Methyl 7-[5-[[1,1'-Biphenyl)-4-yl]methoxy]-3-hydroxy-2-(4-morpholinyl)cyclopentyl]-4-heptenoate A solution of Intermediate 12a (0.7 g) in 9:1 methanol-H$_2$SO$_4$ (20 ml) was stirred at room temperature for 2 h. Solid NaHCO$_3$ was added until pH 7.5–8, followed by water and extraction with ER. The combined extracts were dried, filtered and evaporated to give the title compound as an oil (0.54 g). IR (CHBr$_3$) 3580–3510, 1730 cm$^{-1}$.

Intermediate 15

(endo, anti)-(±)-6-[[4'-Methyl(1,1'-biphenyl)-4-yl]methoxy]-8-(4-morpholinyl)-2-oxabicyclo[3.2.1]octan-3-one Zinc bromide (27 g) in dry THF (180 ml) was stirred under nitrogen at 15°–20° during the addition of p-methylphenylmagnesium bromide [prepared in ether (160 ml) from Mg (3.24 g) and 4-bromotoluene (20.52 g)]. The mixture was stirred at 20° for 2 h. Nickel acetylacetonate (1.8 g) and triphenylphosphine (7.34 g) were taken into THF (40 ml) and stirred under nitrogen during the addition of DIBAL (1 M in hexane, 7 ml). After 5 min. Intermediate 72 (4.75 g) in THF (65 ml) was added followed, after a further 5 min. by the organozinc reagent. The mixture was then stirred at 22° for 30 h, whereupon saturated NH$_4$Cl solution (500 ml) and EA (300 ml) were added. The aqueous solution was adjusted to pH 5–6 with 2 N hydrochloric acid and the layers separated. The aqueous solution was extracted with EA and the combined extracts dried and evaporated. The residue was chromatographed on silica using 7:3 through to 9:1 EA-PE (b.p. 60°–80°) as eluent to give the title compound (3.1 g) as prisms, m.p. 141°–144°.

Intermediate 16

(1α,2β,3α,5α)-(±)-3-Hydroxy-5-[[4'-methyl(1,1'-biphenyl)-4-yl]methoxy]-2-(4-morpholinyl)cyclopentane acetaldehyde A stirred solution of Intermediate 15 (4.5 g) in dry CH$_2$Cl$_2$ (75 ml) at −75° under nitrogen was treated with DIBAL (1.43 M in hexane, 17.4 ml). Stirring was continued for 1 h, whereupon methanol (75 ml) was carefully added and the temperature allowed to rise to ambient. After 17 h, the mixture was filtered and the filtrate evaporated to give the title compound as foam (4.63 g). TLC 9:1 EA-methanol Rf 0.35.

Intermediate 17

(a) (1α,2β,3α,5α)-(±)-3-Hydroxy-5-[[4'-methyl(1,1'-biphenyl)-4-yl]methoxy]-2-(4-morpholinyl)cyclopentanepropanal To a stirred solution of potassium t-butoxide (3.89 g) in dry THF (110 ml) at −5° was added (methoxymethyl)triphenylphosphonium chloride (11.89 g) portionwise over 15 min. After stirring for 30 min. at −5° to 0° a solution of Intermediate 16 (4.03 g) in dry THF (35 ml) was added. The mixture was stirred at 5° for 15 min. and then at 20° for 1.75 h, quenched with water (7 ml) and the solvents removed in vacuo. The residue was then treated with 2 N hydrochloric acid (20 ml) in acetone (50 ml) at 20° for 3.5 h. Aqueous Na$_2$CO$_3$ was added to give a solution of pH 8 which was then diluted with water (100 ml) and extracted with EA (3×75 ml). The combined extracts were dried and evaporated and the residue chromatographed on silica (400 g) using 97:3 through to 9:1 EA-methanol as eluent to give the title compound as an oil (4.33 g). IR (Neat) 3400(br.), 1720 cm$^{-1}$.

The following compounds were prepared by a similar procedure:

(b) (1α,2α,3α,5α)-(±)-5-[[1,1'-Biphenyl)-4-yl]methoxy]-3-hydroxy-2-(4-morpholinyl)cyclopentanepropanal, m.p. 114°–116° from Intermediate 4c.

(c) (1α,2β,3α,5α)-(±)-5-[[1,1'-Biphenyl)-4-yl]methoxy]-3-hydroxy-2-(1-piperidinyl)cyclopentanepropanal, from Intermediate 4e. IR (CHBr$_3$) 3500–3400(br.), 1718 cm$^{-1}$.

(d) (1α,2β,3α,5α)-(±)-5-Decyloxy-3-hydroxy-2-(4-morpholinyl)cyclopentanepropanal, from intermediate 4g. Purification by chromatography using EA through to 95:5 EA-methanol as eluents. IR (Neat) 3530, 1723 cm$^{-1}$.

Intermediate 18

[1α(Z),2β,3α,5α](±)-7-[3-Hydroxy-5-[[4'-methyl(1,1'-biphenyl)-4-yl]methoxy]-2-(4-morpholinyl)cyclopentyl]-4-heptenoic acid (3-Carboxypropyl)triphenylphosphonium bromide (12.9 g) was added to a solution of potassium t-butoxide (6.73 g) in dry THF (170 ml) and the resultant suspension stirred at 20° for 35 min. A solution of Intermediate 17a (4.23 g) in THF (40 ml) was added and stirring continued at 20° for 2 h. Water (5 ml) was then added, the solvent removed in vacuo and the residue taken into water (300 ml) and adjusted to pH 12 with 2 N NaOH. Non-acidic material was extracted with EA (2×100 ml) and the aqueous solution then re-adjusted to pH 6.5 with 2 N hydrochloric acid. This solution was extracted with EA (3×100 ml) and the combined extracts dried and evaporated to give the title compound as an oil (3.97 g). IR (CHBr$_3$) 3580, 3500, 1720, 1710 cm$^{-1}$.

Intermediate 19

(1α,2β,3β,5β)-(±)-4-[3-[[4'-Methoxy(1,1'-biphenyl)-4-yl]methoxy]-2-(3-methoxy-2-propenyl)-5-[(tetrahydro-2H-pyran-2-yl)oxy]cyclopentyl]morpholine NaH (74% dispersion in oil, 316 mg) was added to a solution of Intermediate 8 (1.11 g) and 4-(bromomethyl)4'-methoxy(1,1'-biphenyl) (2.86 g) in dry DMF (15 ml) under nitrogen at 0°. The mixture was stirred at room temperature for 2h whereupon NaH (74%, 52 mg) was added and the stirring continued for 1h. The mixture was poured into aqueous NH$_4$Cl (150 ml) and extracted with CHCl$_3$ (4×60 ml). The dried organic layers were evaporated and the residue chromatographed on silica (400 g) using 8:2 ER-PE (b.p. 60°–80°) through to ER as eluent to give the title compound as an oil (1.17 g). IR (CHBr$_3$) 1675, 1245 cm$^{-1}$.

Intermediate 20

(1α,2β,3α,5α)-(±)-[3-Hydroxy-5-[[4'-methoxy(1,1'-biphenyl)-4-yl]methoxy]-2-(4-morpholinyl)cyclopentanepropanal A solution of Intermediate 19 (2.99 g) in 2 N hydrochloric acid (25 ml), acetone (50 ml) and $CH_2Cl_2$ (7 ml) was stirred for 30 min. The mixture was poured into 8% $NaHCO_3$ solution (200 ml) and extracted with $CH_2Cl_2$ (3×85 ml). The dried organic layers were evaporated and the residue chromatographed on silica (100 g) using ER through to 4:1 ER-methanol as eluent to give the title compound as an oil (2.09 g). IR ($CHBr_3$) 3600–3500(br.), 2725, 1720 $cm^{-1}$.

Intermediate 21

[1α(Z),2β,3α,5α]-(±)-7-[3-Hydroxy-5-[[4'-methoxy(1,1'-biphenyl)-4-yl]methoxy]-2-(4-morpholinyl)cyclopentyl]4-heptenoic acid (4-Carboxypropyl)triphenylphosphonium bromide (3.9 g) and potassium t-butoxide (2.04 g) in dry THF (90 ml) were stirred at room temperature for 15 min. A solution of Intermediate 20 (2 g) in dry THF (40 ml) was added and the mixture stirred for 2h. Water (30 ml) was added and the solvent evaporated. The residue was poured into 0.3 N NaOH (150 ml) and washed with EA. The basic layer was neutralised by the dropwise addition of 5 N hydrochloric acid and then extracted with $CH_2Cl_2$ (70 ml). The pH was adjusted to 6.5 and the aqueous layer re-extracted with $CH_2Cl_2$ (70 ml). The combined $CH_2Cl_2$ layers were dried and evaporated to give the title compound as a foam (1.66 g). IR ($CHBr_3$) 3590, 3500, 1720 $cm^{-1}$.

Intermediate 22

(a) Methyl 4-(Thien-2-yl)benzoate

The Grignard reagent from 2-bromothiophene (17.5 g) and Mg (2.7 g) in dry ER (200 ml) was added to a stirred solution of anhydrous $ZnBr_2$ (22.5 g) in dry THF (200 ml) at 5°.

Simultaneously a solution of bis(triphenylphosphine)palladium (II) dichloride (1 g) in THF (200 ml) was treated with DIBAL in hexane (1.43 M, 2 ml) at room temperature under nitrogen. After 5 min a solution of methyl p-bromobenzoate (5 g) in ER (50 ml) was added followed after a further 5 min by the organozinc reagent described above. The mixture was stirred at room temperature for 18h and then poured into $NH_4Cl$ solution and extracted with EA. The combined extracts were dried and evaporated, and the residue chromatographed on silica using 1:20 through to 1:1 EA-PE as eluent. The title compound was further purified by crystallisation from PE (b.p. 60°–80°) (2.8 g), m.p. 141°–142°.

The following compound was prepared in a similar manner:

(b) Methyl 3'-Methoxy(1,1'-biphenyl)-4-carboxylate, m.p. 52°–54° from 3-bromoanisole and methyl p-bromobenzoate using the catalyst prepared from DIBAL, nickel acetylacetonate and triphenylphosphine. The product was purified by chromatography using 1:4 EA-PE (b.p. 60°–80°) as eluent.

Intermediate 23

(a) 4-(Thien-2-yl)benzene methanol

To a stirred suspension of $LiAlH_4$ (2.28 g) in THF (200 ml) at room temperature was added dropwise a solution of Intermediate (22a) (6.6 g) in THF (50 ml). The mixture was heated under reflux for 2h and then stirred at room temperature for 16h. EA (10 ml) was carefully added, followed by 2 N hydrochloric acid (100 ml). The THF was removed in vacuo and the residue extracted with ER. The combined extracts were dried, filtered and concentrated. Crystallisation of the residue from cyclohexane gave the title compound (4.5 g) as plates, m.p. 115°.

The following compounds were prepared in a similar manner:

(b) 3-[(1,1'-Biphenyl)-4-yl]propanol, m.p. 73°–74° from 3-[(1,1'-biphenyl)-4-yl]propanoic acid.

(c) [3'-Methoxy(1,1'-biphenyl)-4-yl]methanol, from Intermediate 22b. TLC EA Rf. 0.6.

Intermediate 24

(a) 2-(4-Bromomethylphenyl)thiophene

A solution of Intermediate 23a (4.3 g) in dry $CH_2Cl_2$ (80 ml) was treated with a solution of $PBr_3$ (2.15 ml) in $CH_2Cl_2$ (20 ml) and the mixture stirred for 1h. 10% $NaHCO_3$ solution (100 ml) was added, the organic phase separated, and the aqueous phase further extracted with $CH_2Cl_2$. The combined organic phase was dried, filtered and concentrated to give the title compound (4.6 g) as a solid, m.p. 80°–100°.

The following compounds were prepared by a similar procedure:

(b) 4-Bromomethyl(1,1':4',1")terphenyl, m.p. 213°–215° from 4-[(1,1':4',1")terphenyl]methanol.

(c) 4-Bromomethyl-3'-methoxy(1,1'-biphenyl), from Intermediate 23c. TLC ER Rf 0.58.

Intermediate 25

(a) [1α(E),2β,3α,5α]-(±)-7-[3-Hydroxy-5-[[4'-methyl(1,1'-bipenyl)-4-yl]methoxy]-2-(4-morpholinyl)cyclopentyl]-4-heptenoic acid A solution of Intermediate 18 (1.32 g) and p-toluene sulphinic acid (0.63 g) in dry 1,4-dioxan (60 ml) was heated under reflux in a nitrogen atomosphere for 3.5h. The mixture was diluted with EA (80 ml), washed with pH 6 phosphate buffer (50 ml), dried and evaporated. The residue was chromatographed on silica using 9:1 EA-methanol as eluent to give the title compound as an oil, which on trituration with ER crystallised (0.63 g), m.p. 108°–111°.

The following compounds was prepared in a similar manner:

(b) [1α(E),2β,3α,5α]-(±)-7-[5-[[(1,1'-Biphenyl)-4-yl]methoxy]-3-hydroxy-2-(4-morpholinyl)cyclopentyl]4-heptenoic acid, from Intermediate 12a. Purification by chromatography using 9:1 EA-methanol as eluent. TLC 85:15 ER-methanol Rf 0.24.

Intermediate 26

[1α(Z),2β,3α,5α]-(±)-7-[5-[[1,1'-Biphenyl)-4-yl]methoxy]-3-hydroxy-2-(4-morpholinyl)cyclopentyl]-4-heptenol A solution of Intermediate 12a (1 g) in dry THF (10 ml) was added dropwise under nitrogen to a stirred suspension of $LiAlH_4$ (0.16 g) in dry THF (10 ml) and the mixture heated under reflux for 2h. After cooling 1:1 water in THF (10 ml) was added followed by 5 N NaOH (10 ml) and the mixture extracted with EA (3×20 ml). The combined extracts were dried, concentrated and the residue chromatographed on silica using 95:5 ER-methanol as eluent to give an oil which slowly crystallised (0.71 g). Recrystallisation from ER-isopentane gave the title compound of m.p. 70°–71.5°.

Intermediate 27

(anti,endo,endo)-(±)-7-(4-Morpholinyl)-5-[(tetrahydro-2H-pyran-2-yl)oxy]bicyclo[2.2.1]heptan-2-ol NaBH$_4$ (2.2 g) was added in portions to a stirred solution of Intermediate 69 (17 g) in dry methanol (250 ml) at 0°. After 30 min the mixture was poured into saturated NH$_4$Cl solution (350 ml) and extracted with ER (3×200 ml). The combined extracts were dried, filtered and concentrated to give the title compound as a foam (17.5 g). IR (Neat) 3440(br.), 1120 cm$^{-1}$.

Intermediate 28

(endo,syn,endo)-(±)-5-[[(1,1'-Biphenyl)-4-yl]methoxy]-7-(4-morpholinyl)bicyclo[2.2.1]heptan-2-ol A solution of Intermediate 2c (20.1 g) in 10% concentrated H$_2$SO$_4$ in methanol (60 ml) was stood at room temperature for 1h. The solution was neutralised with solid NaHCO$_3$ and extracted with CH$_2$Cl$_2$ (3×200 ml). The combined extracts were dried, filtered and concentrated to give the title compound as a solid (17 g), m.p. 138°–140°.

Intermediate 29

(endo,syn)-(±)-[[(1,1'-Biphenyl)-4-yl]methoxy]-7-(4-morpholinyl)bicyclo[2.2.1]heptan-2-one A mixture of dry dimethylsulphoxide (13.5 ml) and dry CH$_2$Cl$_2$ (50 ml) was added under nitrogen to a solution of oxalyl chloride (15.2 ml) in dry CH$_2$Cl$_2$ (25 ml) at −78° and the resultant activated complex stirred for 15 min. A solution of Intermediate 28 (15 g) in dry CH$_2$Cl$_2$ (50 ml) was added dropwise and stirring continued for 5h. Triethylamine (55.1 ml) in dry CH$_2$Cl$_2$ (50 ml) was added dropwise and the mixture was then allowed to reach room temperature with further stirring for 1.5h. Water (350 ml) was added and the solution extracted with CH$_2$Cl$_2$ (3×200 ml). The combined extracts were dried, filtered and evaporated and the residue chromatographed on silica using ER as eluent. The title compound was obtained as a solid which was further purified by crystallisation from EA-PE (b.p. 60°–80°) to give material (6.67 g) of m.p. 164°–165°.

Intermediate 30

(endo,syn)-(±)-6-[[(1,1'-Biphenyl)-4-yl]methoxy]-8-(4-morpholinyl)-2-oxabicyclo[3.2.1]octan-3-one Peracetic acid (4.33 ml), 6.12 M was added dropwise to a mixture of Intermediate 29 (2 g), sodium acetate (2.17 g), acetic acid (20 ml) and water (10 ml) at 0°. After stirring for 6 days a further quantity of peracetic acid (0.87 ml) was added and stirring continued for 24h. Na$_2$SO$_3$ was added to destroy excess oxidising agent and the mixture was then evaporated to dryness. The residue was neutralised with 8% NaHCO$_3$ solution and extracted with EA (3×75 ml). The combined extracts were dried, filtered and evaporated and the residue chromatographed on silica using 1:1 ER-CH$_2$Cl$_2$ as eluent to give the title compound as a solid (1.5 g), m.p. 244°–246°.

Intermediate 31

[1α(Z),2α,3α,5α]-(±)-Methyl 7-[5-[[1,1'-Biphenyl)-4-yl]methoxy]-3-hydroxy-2-(4-morpholinyl)cyclopentyl]4-heptenoate Prepared as an oil from Intermediate 17a according to the methods described for Intermediates 12a and 14. IR (Neat) 3440 (br), 1730 cm$^{-1}$.

Intermediate 32

[1α(Z),2α,3α,5α]-(±)-Methyl 7-[3-(Acetyloxy)-5-[[(1,1'-biphenyl)-4-yl]methoxy]-2-(4-morpholinyl)cyclopentyl]-4-heptenoate A solution of Intermediate 31 (1.2 g) and acetic anhydride (2 ml) in pyridine (10 ml) was heated at 45° for 18h. The mixture was diluted with ER (50 ml) and then washed with 8% NaHCO$_3$ solution (150 ml). The aqueous solution was re-extracted with ER (100 ml) and the combined organic phase dried and concentrated. The residue was chromatographed on silica using ER as eluent to give the title compound as an oil (0.85 g). IR (CHBr$_3$) 1742 cm$^{-1}$.

Intermediate 33

(a) [1α(Z),2α,3α,5α]-(±)-7-[5-[[(1,1'-Biphenyl)4-yl]methoxy]-3-hydroxy-2-(4-morpholinyl)cyclopentyl]4-heptenoic acid A solution of Intermediate 32 (0.83 g) in methanol (30 ml) containing 2 N NaOH (5 ml) was allowed to stand at room temperature for 2 days. pH 6.5 Buffer (made from 2:3 KH$_2$PO$_4$:Na$_2$HPO$_4$) (30 ml) was added and the solution extracted with CH$_2$Cl$_2$ (2×50 ml). The combined extracts were dried and concentrated and the residue purified from CH$_2$Cl$_2$-PE (b.p. 60°–80°) to give the title compound (0.61 g), m.p. 163°–165°.

The following compound was prepared in a similar manner:

(b) [1α(Z),2β,3α,5α]-(±)-7-[5-[[(1,1'-Biphenyl)-4-yl]methoxy]-3-hydroxy-2-(1-piperidinyl)cyclopentyl]4-heptenoic acid, from Intermediate 58. IR (CHBr$_3$) 3500, 1700, 1598 cm$^{-1}$.

Intermediate 34

[1α(Z),2β,3β,5α]-(±)-7-[5-[[1,1'-Biphenyl)-4-yl]methoxy]-3-hydroxy-2-(4-morpholinyl)cyclopentyl]-4-heptenoic acid A stirred solution of lithium tri-sec-butylborohydride in THF (12 ml, 1 M) under nitrogen at −28° was treated slowly dropwise with a solution of Example 1a (0.6 g) in dry THF (12 ml). After 3h the mixture was poured into 2 N H$_2$SO$_4$ (20 ml) and pH 6.5 phosphate buffer (50 ml) and washed with ER (1×150 ml, 1×50 ml). The aqueous layer was adjusted to pH 6.5 with 2 N NaOH and extracted with EA (2×100 ml). The combined extracts were dried and evaporated, and the residue chromatographed on silica using 4:1 EA-methanol as eluent to give the title compound as a foam (0.35 g). TLC (SiO$_2$) 1:20:79 Acetic acid-methanol-EA Rf 0.17.

Intermediates 35 and 36

(1S,endo)-(+)-Bicyclo[3.2.0]hept-2-en-6-ol (35) and (1R,exo)-(−)-Bicyclo[3.2.0]hept-2-en-6-ol (36)

Bakers yeast (6 kg) and glucose (2.5 kg) in water (24 l) was stirred at 25° for 2h. (±)-Bicyclo[3.2.0]hept-2-en-6-one (120 g) was added dropwise over 30 min. Stirring was maintained for 2.5h whereupon a further quantity of glucose (3.5 kg) and water (4 l) was added. This addition was repeated after 20h and 26h, glucose (4.5 kg) and water (5 l) being added on each occasion.

The reaction mixture was distilled at atmospheric pressure to give about 11 l of aqueous ethanol containing starting material and some product-FRACTION A. Then a steam distillation of the remaining reaction mixture gave 36 l of aqueous distillate which was salted (7.25 kg) and extracted with CH$_2$Cl$_2$(3×10 l). The CH$_2$Cl$_2$ was distilled at atmospheric pressure through a helix filled column (93×5 cm) to leave a residue (about 400 ml)-FRACTION B. FRACTION A was concentrated by distilling off most of the solvent through a helix filled column (50×3 cm). The residue was salted and extracted into CH$_2$Cl$_2$-FRACTION C.

Fractions B and C were combined, dried and the solvent was removed at atmospheric pressure to leave a residue (55 g) which was distilled at 120° C. and 15 mmHg pressure to give an oil (39.8 g). This material was chromatographed on silica using 1:4 ether:isopentane as eluent to give the title compound as ethereal solutions after removal of most the solvent.

Intermediate 35 (26.8 g) 64.5% w/w in ether.
Intermediate 36 (33.4 g) 30.4% w/w in ether.

The bulk of the material was used as above for the next stage. However 2 ml portions of the solutions were taken and distilled at atmospheric pressure in a micro distillation apparatus to give:

Intermediate 35

TLC 4:1 PE-ER Rf 0.3 $[\alpha]_D^{26} = +46.1°$ (CHCl$_3$)

Intermediate 36

TLC 4:1 PE-ER Rf 0.2 $[\alpha]_D^{26} = -73.9°$ (CHCl$_3$).

Intermediate 37

[1R-(exo,endo)]-(−)-2-Bromo-3-hydroxybicyclo[3.2.0]heptan6-one

To a stirred solution of Intermediate 35 (6.64 g) in acetone (220 ml) and water (55 ml) was added glacial acetic acid (0.65 ml) and N-bromosuccinimide (43.22 g) and stirring was maintained for 18h. The mixture was poured into sodium thiosulphate solution (250 ml) and extracted with ER (2×175 ml). The organic layer was washed with 8% NaHCO$_3$ solution (150 ml), dried and evaporated and the residue chromatographed on silica using 1:1 ER-PE as eluent. The title compound was obtained as a solid which crystallised from CCl$_4$ as needles (4.16 g), m.p. 90°-92°. $[\alpha]_D^{20} = -60.8°$ (MeOH).

Intermediate 41

[1R-(endo,anti)]-(+)-5-Hydroxy-7-(4-morpholinyl)-bicyclo-[2.2.1]heptan-2-one

A solution of Intermediate 37 (8.82 g) in CH$_2$Cl$_2$ (85 ml) containing morpholine (15 ml) was stirred at room temperature for 20h. The precipitate was filtered off and washed with CH$_2$Cl$_2$ (100 ml). The combined filtrates were washed with NaHCO$_3$ solution and water (75 ml each) dried and evaporated to give a semi-solid which was chromatographed on silica using EA as eluent. The title compound was obtained as a solid which crystallised from 1:1 EA-PE (b.p. 60°-80°) to give material (6.1 g) of m.p. 137°-139°. $[\alpha]_D^{20} = +55.73°$ (MeOH).

Intermediate 43

[1R-(endo,anti)]-(+)-5-[[(1,1'-Biphenyl)-4-yl]methoxy]-7-(4-morpholinyl)bicyclo[2.2.1]heptan-2-one A mixture of Intermediate 41 (10.45 g), benzyl triethylammonium chloride (1.5 g) and biphenylmethyl bromide (15.3 g) in CH$_2$Cl$_2$ (50 ml) was cooled to 0° whilst NaOH (12 g) in water (20 ml) was added. The two phases were stirred vigorously for 24h at 20°. The mixture was diluted with water (120 ml) and extracted with CH$_2$Cl$_2$ (3×100 ml). The combined extracts were washed with brine (2×50 ml), dried and evaporated, and the residue triturated with ER (100 ml) to give a solid (16 g). The solid was crystallised from isopropyl acetate (120 ml) to give the title compound (9.6 g) as platelets, m.p. 138°-140°. $[\alpha]_D^{21} = +22.12°$ (CHCl$_3$).

Intermediate 44

[1R-(endo,anti)]-(−)-6-[[(1,1'-Biphenyl)-4-yl]methoxy]8-(4-morpholinyl-2-oxabicyclo[3.2.1]octan-3-one Peracetic acid (8.7 ml, 6.12 M) was added dropwise to a stirred solution of Intermediate 43 (5 g) in CH$_2$Cl$_2$ (25 ml) at 0°. The mixture was stirred for 24h while allowing the temperature to rise to ambient. 20% w/w Na$_2$SO$_3$ in water (60 ml) was added dropwise at 0° and the mixture was stirred at room temperature for 0.75h. Iso-propyl acetate (25 ml) was added and the layers were separated. The aqueous layer was extracted with (1:1) isopropyl acetate-CH$_2$Cl$_2$ (2×25 ml), and the combined organic layers were washed with 1 N NaOH (2×50 ml) and brine (50 ml) then dried and evaporated to give a solid (3.3 g). The solid was crystallised from 1:1 EA-PE (80 ml) to give the title compound as prisms (6.9 g), m.p. 147°-148°. $[\alpha]_D^{21.5} = -26.44°$ (CHCl$_3$).

Intermediate 45

[1R-(1α,2β,3α,5α)]-5-[[(1,1'-Biphenyl)-4-yl]methoxy]-3-hydroxy-2-(4-morpholinyl)cyclopentane acetaldehyde A solution of Intermediate 44 (3 g) in dry CH$_3$Cl$_2$ (60 ml) was cooled (−78°) and stirred under nitrogen whilst a solution of DIBAL in hexane (10.7 ml, 1.43 M) was added dropwise. Methanol (60 ml) was added dropwise at −78° and the cooling bath was removed. After stirring at room temperature for 2h the precipitate was filtered off and was washed well with methanol. The combined filtrates were evaporated in vacuo and the residue was dissolved in CH$_2$Cl$_2$ (100 ml), dried, filtered and evaporated to give the title compound as a foam (2.95 g). IR (CHBr$_3$) 3580, 1718 cm$^{-1}$.

Intermediate 46

[1R-(1α,2β,3α,5α)]-5-[[(1,1'-Biphenyl)-4-yl]methoxy]3-hydroxy-2-(4-morpholinyl)cyclopentanepropanal (Methoxymethyl)triphenylphosphonium chloride (7.15 g) was added to a stirred solution of potassium tert.-butoxide (2.35 g) in dry THF (40 ml) under nitrogen. After 15 min a solution of Intermediate 45 (2.75 g) in dry THF (20 ml) was added dropwise and stirring continued for 30 min.

The reaction mixture was poured into 2 N hydrochloric acid (50 ml) at 0° and was stirred at 10°-15° for 1.5h. The mixture was adjusted to about pH 10 was saturated K$_2$CO$_3$ solution and extracted with CH$_2$Cl$_2$ (3×100 ml). The combined extracts were washed with brine (100 ml), dried and evaporated and the residue chromatographed on silica using 9:1 EA-methanol as eluent to give the title compound as a foam (2.47 g). TLC 9:1 EA-methanol Rf 0.3.

Intermediate 47

[1R-[1α(Z),2β,3α,5α]]-(+)-7-[5-[[(1,1'-Biphenyl)-4-yl]methoxy]-3-hydroxy-2-(4-morpholinyl)cyclopentyl]-4-heptenoic acid, hydrochloride Dry THF (90 ml) was added to a stirred mixture of potassium tert.-butoxide (2.46 g) and 3-(carboxypropyl)-triphenylphosphonium bromide (4.6 g) under nitrogen. After about 30 min Intermediate 46 (2.25 g) in dry THF (50 ml) was added dropwise and stirring continued for 2.5h. Water (25 ml) was added and most of the THF was removed in vacuo. The residue in water (50 ml) and 2 NaOH (20 ml) was extracted with EA (2×50 ml). The aqueous layer was adjusted to pH 6 with buffer (1 M $KH_2PO_4$ 3 parts, 1 M $Na_2HPO_4$ 1 part) and was extracted with $CH_2Cl_2$ (3×50 ml). The combined extracts were washed with brine, dried and evaporated to give a foam (2.7 g). This material was dissolved in EA (100 ml) and treated with an excess of ethereal hydrogen chloride. After cooling at 0° for 16h the salt was collected and washed with 1:1 ER-EA (25 ml) followed by ER (40 ml). Crystallisation from 5:1 EA-methanol gave the title compound (1.6 g) as prisms, m.p. 152°–153°. $[\alpha]_D^{21} = +54°$ ($CHCl_3$).

Intermediate 51

(endo,anti)-(±)-7-Azido-5-hydroxybicyclo[2.2.1]heptan-2-one

A solution of (exo,endo)-(±)-3-acetoxy-2-bromobicyclo[3.2.0]heptan-6-one (50 g) of potassium t-butoxide (27.25 g) in THF (1.5 l) was stirred at −75° for 1 h. The solution was allowed to warm to 0° and a solution of sodium azide (16.45 g) in water (600 ml) was added and stirring continued at 20° for 18 h.

The two layers were separated and ether was added to the organic layer which was washed with water (2×250 ml). The combined aqueous layers were extracted with ER (2×250 ml). The combined organic layers were dried and evaporated to give a gum (28.1 g). A solution of the gum in methanol (225 ml) was stirred with $K_2CO_3$ (18.37 g) for 3.5 h at room temperature. The mixture was filtered and the filtrate was evaporated in vacuo to give a solid which was taken into ER (150 ml) and washed with water (150 ml). The aqueous layer was extracted with ER (3×125 ml) and the combined organic layers were dried and evaporated to give an oil (24.5 g) which was chromatographed on silica. Elution with 2:1 ER-PE gave an oil (18.7 g) which was triturated with ER to give the title compound as a solid (14.6 g), m.p. 72°–74°.

Intermediate 52

(3aα,4β,5α,6aα)-(±)-4-Azido-hexahydro-5-hydroxy-2H-cyclopenta(b)furan-2-one

40% Peracetic acid (64.35 ml) was added to a cooled (0°) stirred solution of Intermediate 51 (12.9 g) and sodium acetate (31.2 g) in acetic acid (155 ml) and water (15.5 ml) and the resulting solution then stirred at ambient temperature for 24 h. Excess $Na_2SO_3$ solution was added to the cooled solution and stirring continued for 1 h. After evaporation in vacuo the residue was dissolved in 5 N NaOH solution (400 ml) with cooling and the solution stirred for 0.5 h. Concentrated hydrochloric acid (30 ml) was added with cooling and the solution was continuously extracted with $CH_2Cl_2$ (600 ml) for 18 h. The organic extracts were washed with 2 N $Na_2CO_3$ solution (100 ml) and brine (100 ml), dried and evaporated to give a solid (3.5 g). A portion (1 g) was recrystallised from ER-PE (b.p. 60°–80°) to give the title compound (816 mg), m.p. 73°–74°.

Intermediate 53

(3aα,4β,5β,6aα)-(±)-4-Azido-hexahydro-5-[(tetrahydro-2H-pyran-2-yl)oxy]-2H-cyclopenta(b)furan-2-one Dihydropyran (6.1 ml) was added to a cold (−20°) stirred solution of p-toluenesulphonic acid (0.685 g) and Intermediate 52 (6.63 g) in $CH_2Cl_2$ (35 ml). After 2 h at −20° the mixture was poured into 8% $NaHCO_3$ solution (300 ml). The organic layer was separated and the aqueous layer extracted with $CH_2Cl_2$ (3×100 ml). The combined extracts were washed with brine (200 ml), dried and evaporated in vacuo to give an oil (13.23 g) which was purified by chromatography on silica. Elution with 2:1 ER-PE (b.p. 60°–80°) gave the title compound as an oil (5.39 g). IR (Neat) 2100, 1780 cm$^{-1}$.

Intermediate 54

(a) (3aα,4β,5α,6aα)-(±)-4-Amino-hexahydro-5-[(tetrahydro-2H-pyran-2-yl)oxy]-2H-cyclopenta(b)furan-2-one A solution of Intermediate 53 (28.4 g) in ethanol (175 ml) was hydrogenated at atmospheric pressure over pre-reduced 10% palladium oxide on charcoal (5.3 g) at 20° for 24 h. The mixture was filtered ('Hyflo') and the filtrate evaporated to give an oil (24.1 g). IR ($CHBr_3$) 3370, 3300, 1762 cm$^{-1}$.

Intermediate 55

(3aα,4α,5β,6aα)-(±)-Hexahydro-5-[(tetrahydro-2H-pyran-2-yl)oxy]-4-(4-thiomorpholinyl)-2H-cyclopenta(b)furan-2-one A mixture of Intermediate 54 (6 g), anhydrous $NaHCO_3$ (5.2 g), NaI (9.72 g) and bis-(2-chloroethyl)-sulphide (5.15 g) in acetonitrile (250 ml) was heated under reflux for 18 h. The solvent was removed in vacuo and the residue in water (200 ml) was extracted with EA (4×200 ml). The combined extracts were washed with brine (200 ml), dried and evaporated to give an oil (10.2 g) which was purified by chromatography on silica. Elution with ER and then 3:97 methanol-ER gave a solid (4.8 g). A portion was crystallised from ER-PE to give the title compound, m.p. 83°–84°.

The following compound was prepared in a similar manner:

(b) (3aα,4α,5β,6aα)-(±)-4-(hexahydro-1,4-oxazepin-4-yl)-5-[(tetrahydro-2H-pyran-2-yl)oxy]-2H-cyclopenta(b)furan-2-one, m.p. 68.5°–72.5° from Intermediate 54. Purification of chromatography using 85:15 ER-methanol as eluent.

Intermediate 56

(anti,endo)-(±)-7-(1-Piperidinyl)-5-[(tetrahydro-2H-pyran-2-yl)oxy]bicyclo[2.2.1]heptan-2-one Piperidine (64.1 ml) was added dropwise to a solution of (exo,endo)-(±)-2-bromo-3-[(tetrahydro-2H-pyran-2-yl)oxy]bicyclo[3.2.0]heptan-6-one (75 g) in high purity acetone (250 ml) at 0°. The mixture was stirred in the dark for 24 h and then filtered. The filtrate was washed with water (2×150 ml), and the aqueous solution extracted with ER (3×200 ml). The combined organic layers were dried, filtered and evaporated to give the title compound as an oil (77.2 g). TLC 7:3 ER-PE Rf 0.18.

Intermediate 57

(endo,anti)-(±)-5-Hydroxy-7-(1-piperidinyl)bicyclo[2.2.1]-heptan-2-one, hydrochloride Ethereal hydrogen chloride (20 ml) was added dropwise to a solution of Intermediate 56 (77.2 g) in methanol (300 ml) at 0°. After stirring for 1.5 h at room temperature the solvent was removed in vacuo, and the residue triturated with iso-propanol to give the title compound as a solid (52 g), m.p. 246°–248°.

Intermediate 58

[1α(Z),2β,3α,5α]-(±)-Methyl 7-[5-[[(1,1'-Biphenyl)-4-yl]methoxy]-3-hydroxy-2-(1-piperidinyl)cyclopentyl]-4-heptenoate Prepared as an oil from Intermediate 17c according to the methods described for Intermediates 12a and 14. Purification by chromatography using 9:1 EA-methanol as eluent. IR (CHBr$_3$) 3520, 1725 cm$^{-1}$.

Intermediate 59

(a) (1α,2α,3β,4α)-(±)-2-(3-Methoxy-2-propenyl)-4-[(tetrahydro-2H-pyran-2-yl)oxy]-3-(4-thiomorpholinyl)-cyclopentanol, S-dioxide A solution of Intermediate 7b (12.1 g) in methanol (80 ml) containing 1 N NaOH (60 ml) was stirred at room temperature for 5 h. The mixture was poured into brine (650 ml) and extracted with CH$_2$Cl$_2$ (5×150 ml). The combined extracts were dried, filtered and concentrated to give an oil, which was chromatographed on silica using 13:7 EA-PE (b.p. 60°-80°) through to EA as eluent to give the title compound as an oil (8.38 g). IR (Neat) 3510 (br), 1650 cm$^{-1}$.

The following compound was prepared by a similar procedure:

(b) (1α,2α,3β,4α)-(±)-3-(Hexahydro-1,4-oxazepin-4-yl)-2-(3-methoxy-2-propenyl)-4-[(tetrahydro-2H-pyran-2-yl)oxy]cyclopentanol, from Intermediate 7c IR (CHBr$_3$) 3500, 1655 cm$^{-1}$.

Intermediate 60

3-[(1,1'-Biphenyl)-4-yl]propanol,4-methylbenzenesulphonate

A stirred solution of Intermediate 23b (4.28 g) in pyridine (40 ml) at 0° was treated portionwise with p-toluene sulphonyl chloride (7.71 g) over 1 h. Stirring was continued at 0° for 7 h when water (20 ml) was added and the mixture allowed to warm to room temperature with stirring for a further 1 h. The mixture was partitioned between 2N.H$_2$SO$_4$ (250 ml) and ER (250 ml), the layers separated and the organic phase washed with a further quantity of 2N.H$_2$SO$_4$ (2×250 ml). The organic phase was then washed with 2N.NaOH (3×100 ml), water (2×100 ml) and dried. Evaporation of the solvent gave the title compound as a solid (4.95 g), m.p. 86°-87°.

Intermediate 61

(3aα,4α,5β,6aα)-(±)-Hexahydro-5-hydroxy-4-(4-thiomorpholinyl)-2H-cyclopenta(b)furan-2-one, S-dioxide, hydrochloride A solution of (endo,anti)-(±)-6-(phenylmethoxy)-8-(4-thiomorpholinyl)-2-oxabicyclo[3.2.1]octan-3-one, S-dioxide (10 g) in ethanol (60 ml) and water (40 ml) containing concentrated hydrochloric acid (40 ml) was hydrogenated over pre-reduced 10% palladium oxide on charcoal (5 g, 50% dispersion in water) in ethanol (40 ml). The mixture was filtered and the filtrate evaporated in vacuo to give the title compound as a solid (8.55 g), m.p. above 230° (dec.) (from water-ethanol).

Intermediate 62

(3aα,4α,5β,6aα)-(±)-Hexahydro-5-[(tetrahydro-2H-pyran-2-yl)oxy]-4-(4-thiomorpholinyl)-2H-cyclopenta(b)furan-2-one, S-dioxide Dihydropyran (3.1 ml) was added to a stirred solution of the free base of Intermediate 61 (1.56 g) and p-toluene sulphonic acid monohydrate (1.17 g) in dry DMF (30 ml) at −10°. The mixture was allowed to reach ambient temperature and stirring continued for 18 h, whereupon it was poured into saturated aqueous NaHCO$_3$ solution (50 ml), extracted with EA (4×100 ml), washed with water, dried, filtered and concentrated. The residue was chromatographed using 19:1 ER-methanol as eluent to give the title compound as a viscous oil (1.89 g). IR (CHBr$_3$) 1762 cm$^{-1}$.

Intermediate 63

(3aα,4α,5β,6aα)-(±)-Hexahydro-5-[(tetrahydro-2H-pyran-2-yl)oxy]-4-(4-thiomorpholinyl)-2H-cyclopenta(b)furan-2-ol, S-dioxide A solution of Intermediate 62 (1 g) in CH$_2$Cl$_2$ (25 ml) at −70° under dry nitrogen was stirred during the addition of DIBAL (1 M in hexane, 8.7 ml). After 1.5 h at −70°, methanol (25 ml) was carefully added and the mixture was then allowed to rise to ambient temperature whereupon stirring was continued for 18 h. The mixture was filtered through 'Hyflo' and the filtrate evaporated to give the title compound as an oil (0.95 g).

Analysis Found: C, 53.2; H, 7.6; N, 3.5. C$_{16}$H$_{27}$NO$_6$S requires: C, 53.2; H, 7.5; N, 3.9%.

Intermediate 66

[4'Methyl-(1,1-biphenyl)-4-yl]methanol

4-Methyl-(1,1'-biphenyl)-4-carboxylic acid, methyl ester (1.43 g) in ER (25 ml) and THF (25 ml) was added over 5 min to LiAlH$_4$ (420 mg) in ER (25 ml). The mixture was stirred at room temperature for 1 h and then cooled in ice. Aqueous NaOH (1 M, 2.1 ml) was added and after stirring (15 min) excess anhydrous Na$_2$SO$_4$ was added. The mixture was filtered and the filtrate evaporated to give a solid. Crystallisation from cyclohexanemethanol gave the title compound (1.04 g) m.p. 128°-31°.

Intermediate 67

4-Bromomethyl-4'-methyl(1,1'-biphenyl)

To a cold (0°) solution of Intermediate 66 (0.917 g) in dry CH$_2$Cl$_2$ (14 ml) was added PBr$_3$ (0.29 ml).

After stirring for 1 h at 0°, 8% NaHCO$_3$ solution (30 ml) was added and the layers separated. The aqueous layer was extracted with CH$_2$Cl$_2$ (2×30 ml), dried and evaporated to give a solid (0.99 g). Crystallisation from PE (b.p. 60°-80°) afforded the title compound (0.91 g) m.p. 100°-102°.

Intermediate 68

4-Bromomethyl-4'-chloro-1,1'-biphenyl

4'-Chloro(1,1'-biphenyl)-4-methanol (5.8 g) was converted into the title compound (6.8 g), m.p. 64°-66° by the method for the preparation of the Intermediate 67.

Intermediate 69

(±)-7-anti-(4-Morpholinyl)-5-endo-[tetrahydro-2H-pyran-2-yl)oxy]bicyclo[2.2.1]heptan-2-one Morpholine (76 ml) was added dropwise over 15 mins to a stirred solution of 2-exo-bromo-3-endo[(tetrahydro-2H-pyran-2yl)oxy]bicyclo[3.2.0]heptan-6-one (100.8 g) in acetone (500 ml) at 0°. After 2 h at 5° the mixture was stirred at 20° for 18 h and then filtered. Evaporation of the filtrate gave an oil which was taken into ER (350 ml), filtered and washed (water, 2×100 ml). The ethereal solution was dried, filtered and evaporated to give the title compound as a solid. Purification from PE gave material (85.5 g) of m.p. 86°-88°.

Intermediate 70

(±)-5-end-Hydroxy-7-anti-(4-morpholinyl)bicyclo[2.2.1]-heptan-2-one, hydrochloride To a stirred solution of Intermediate 69 (96.4 g) in methanol (600 ml) was added an ethereal solution of HCl (240 ml) and the mixture stirred at 20° for 2.5 h (pH 1.5-2). Filtration followed by evaporation of the filtrate gave an oil which solidified on trituration with EA (2×200 ml). Coloured impurities were removed by extraction with boiling isopropanol to leave the title compound as a solid (70.6 g), m.p. 181°-182°.

Intermediate 71

(±)-5-endo-(4-Bromophenylmethoxy)-7-anti-(4-morpholinyl)-bicyclo[2.2.1]heptan-2-one Aqueous NaOH solution (10 N; 200 ml) was added to a solution of the free base of Intermediate 70 (21.1 g), benzyltriethylammonium chloride (4 g) and 4-bromobenzyl bromide (27.5 g) in $CH_2Cl_2$ (400 ml) and the mixture stirred vigorously for 4 h. A further portion of 4-bromobenzylbromide (9 g) was then added and stirring continued for 68 h. Water (200 ml) was added and the layers separated. The aqueous layer was extracted with EA (2×75 ml), washed with water, dried and evaporated to give an oil (48 g) which solidified on standing. Excess alkylating agent was removed by triturition with PE (b.p. 60°-80°) and crystallisation from EA-PE (b.p. 60°-80°) then gave the title compound (34.1 g) as a solid, m.p. 130°-131°.

Intermediate 72

(±)-6-endo-(4-Bromophenylmethoxy)-8-anti-(4-morpholinyl)-2-oxabicyclo[3.2.1]octan-3-one Intermediate 71 (13.2 g) in acetic acid (110 ml) and water (55 ml) containing $CH_3COONa.3H_2O$ (23.7 g) was cooled (ca. 5°-10°) and stirred during the dropwise addition of peracetic acid (6.1 M; 28.5 ml). The resulting solution was stirred at 20° for 48 h when 10% $Na_2SO_3$ solution (200 ml), was added, maintaining the temperature of the mixture at 10°-15°. After 1.5 h solvents were removed in vacuo at 35°, the residue taken into water (150 ml) and basified to pH 9 with $Na_2CO_3$ solution. Extraction with EA (3×200 ml) followed by drying and evaporation gave a solid which crystallised from EA to give the title compound (5.49 g), m.p. 154°-156°.

Intermediate 77

[1α(Z/E),2β,3α,5α]-(±)-7-[5-[[(1,1'-Biphenyl)-4-yl]methoxy]-3-hydroxy-2-(4-morpholinyl)cyclopentyl]-4-bromo-4-heptenoic acid To a stirred solution of potassium tert-butoxide (6.06 g) in dry THF (140 ml) at −70° was added (4-carbethoxypropyl)triphenylphosphonium bromide (22.16 g). After 0.5 h at −70° a solution of bromine in $CH_2Cl_2$ (25% v/v, 6.7 ml) was added dropwise and then stirring maintained for 0.9 h. A solution of Intermediate 6 (4.09 g) in THF (30 ml) was then added and, after 0.5 h, the temperature of the mixture allowed to rise to 0° over 1 h. 2 N NaOH (60 ml) and methanol (60 ml) were added and stirring continued at 20° for 4 h. After evaporation in vacuo the residue was taken into water (200 ml) and adjusted to pH 12 with 2 N NaOH. Non-acidic material was removed by extraction with EA (1×100 ml, 2×50 ml), and the aqueous phase then re-adjusted to pH 6 with 2 N hydrochloric acid. Extraction with EA (4×60 ml), drying and concentration gave the title compounds as a foam (5.23 g). IR ($CHBr_3$) 3500, 1725, 1710 cm$^{-1}$.

Intermediate 78

(1α,2β,3α,5α)-(±)-7-[5-[[(1,1'-Biphenyl)-4-yl]methoxy]-3-hydroxy-2-(4-morpholinyl)cyclopentyl]-4-heptynoic acid, hydrochloride To a stirred solution of Intermediate 77 (2 g) in THF (15 ml) at 0° was added potassium tert-butoxide (2.4 g) in DMSO (15 ml). The mixture was stirred at 0° for 0.5 h and at 20° for 1.5 h whereupon water (200 ml) was added and the mixture extracted with EA (1×50 ml). The aqueous solution was adjusted to pH 6 with 2 N hydrochloric acid and extracted with EA (3×60 ml). The combined extracts were washed with water (3×60 ml), dried and evaporated to give an oil, which was purified by chromatography on silica (130 g) using 4:1 EA-methanol as eluent to give a foam (0.65 g). A sample was treated with ethereal hydrogen chloride to give the title compound. Crystallisation from EA gave material of m.p. 162°-163.5°.

Intermediate 79

(1α,2β,5α)-(±)-[5-[[(1,1'-Biphenyl)-4-yl]methoxy]-2-(4-morpholinyl)-3-oxo-cyclopentyl]-4-heptynoic acid Prepared from the free base of Intermediate 78 according to the procedure described for Example 3a. Purification by chromatography using ER through to 98:2 ER-methanol as eluent. Crystallisation from ER-PE (b.p. 60°80°) gave material of m.p. 90°-93°.

Intermediate 80

(endo,anti)-(±)-5-Decyloxy-7-(4-morpholiyl)bicyclo[2.2.1]heptan-2-one

Sodium hydride (46% dispersion in oil, 0.522 g) was added portionwise over 10 min to a stirred solution of Intermediate 1 (1.06 g) and decyl tosylate (2.34 g) in dry DMF (10 ml) under dry nitrogen at room temperature. The mixture was stirred for 5 h, poured into water (50 ml) and extracted with ER (50 ml, 2×25 ml). The combined extracts were washed with water (25 ml), dried and concentrated to give a solid. Crystallisation from PE gave the title compound (0.59 g), m.p. 64°-65°.

EXAMPLE I (a) [1α(Z),2β,5α]-(±)-7-[5-[[(1,1'-Biphenyl)-4-yl]methoxy]-2-(4-morpholinyl)-3-oxocyclopentyl]-4-heptenoic acid Method I To a cold (−11°) stirred solution of Intermediate 12a) (920 mg) and triethylamine (2.14 ml) in $CH_2Cl_2$ (10 ml) and DMSO (10 ml) was added pyridine-sulphur trioxide complex (915 mg) in DMSO (10 ml). Stirring was maintained at 25° C. for 3 h whereupon water (10 ml) was added and the $CH_2Cl_2$ evaporated. To the resulting suspension a solution of citric acid (1.07 g) in water (10 ml) was added. The mixture was extracted with EA, the combined extracts dried and concentrated. The residual oil was chromatographed on silica using ER as eluent to give the title compound as an oil which slowly crystallised (0.37 g). Recrystallisation of a sample from ER-isopentane at 0° gave material of m.p. 77.5°-80°, IR (Nujol) 3350-2400 (br), 1735, 1705 cm$^{-1}$; whereas recrystalisation above 5° gave a different polymorphic form of m.p. 98°-100.5°, IR (Nujol) 3400-2300 (br), 1735, 1702, 1250, 1005 cm$^{-1}$. Analysis found: C, 72.9; H, 7.4; N, 2.9. $C_{29}H_{35}NO_5$ requires; C, 72.9; H, 7.4; N, 2.9%

Method 2

Jones reagent (0.54 ml, 2.67 M) was added to a mixture of Intermediate 26 (0.25 g) and 'Hyflo' (1 g) in acetone (10 ml) and stirred for 1 h. Isopropanol (1 ml) was added, the mixture filtered and the filtrate washed with pH 5 buffer (2×10 ml). After drying and evaporation the residue was purified by chromatography on silica using ER as eluent to give the title compound (0.024 g).

Method 3

From Intermediate 33a) by the procedure described under Method 2.

Method 4

From Intermediate 34 by the procedure described under Method 2.

Method 5

A suspension of 5% Pd on CaCO$_3$ poisoned with lead (70 mg) in EA (5 ml) containing triethylamine (0.2 ml) was hydrogenated at 21° and atmospheric pressure for 0.5 h. A solution of Intermediate 79 (36 mg) in EA (4 ml) was added and the hydrogenation continued for 2h. The mixture was filtered, diluted with ER (20 ml) and washed with pH 6 phosphate buffer solution (30 ml). Evaporation of the dried ethereal solution gave a solid (35 mg) which crystallised from ER-PE (b.p. 60°–80°) to give the title compound (23 mg), m.p. 95°–98°.

The following compounds were prepared by the procedure described for Method 1.

(b) [1α(Z), 2β,5α]-(±)-8-[5-[[(1,1′-Biphenyl)-4-yl]methoxy]-2-(4-morpholinyl)-3-oxocyclopentyl]-5-octenoic acid, m.p. 118°–120° from Intermediate 13.

Analysis found: C, 73.6; H, 7.7; N, 2.9. C$_{30}$H$_{37}$NO$_5$ requires; C, 73.3; H, 7.6; N, 2.9%.

(c) [1α(Z), 2β, 5α]-(±)-7-[2-(4-Morpholinyl)-5-(2-naphthalenylmethoxy)-3-oxocyclopentyl]-4-heptenoic acid from Intermediate 12b. Purification by chromatography using ER as eluent IR (CHBr$_3$) 3600–2300(br), 1735, 1702 cm$^{-1}$ Analysis Found: C, 71.1; H, 7.5; N, 3.2 C$_{27}$H$_{35}$NO$_5$ requires: C, 71.8; H, 7.4; N, 3.1%

(d) [1α(Z), 2β, 5α]-(±)-7-[5-[4-(1,1-Dimethylethyl)-phenylmethoxy]-2-(4-morpholinyl)-3-oxocyclopentyl]-4-heptenoic acid, from Intermediate 12d. Purification by chromatography using ER as eluent. IR (CHBr$_3$) 3500, 1738, 1705 cm$^{-1}$ TLC 95:5 ER-methanol R$_f$ 0.53

(e) [1α(Z), 2β, 5α]-(±)-7-[5-[4-Methylthio(phenylmethoxy)]-2-(4-morpholinyl)-3-oxocyclopentyl]-4-heptenoic acid, compound with piperazine (2:1), from Intermediate 12j.

The acid was purified by chromatography using ER as eluent. The title compound (106 mg) crystallised from a solution of the acid (168 mg) and piperazine (25 mg) in ER (5 ml) to give material of m.p. 75°–76.5°. IR (CHBr$_3$) 1735, 1590 cm$^{-1}$ (f) [1α(Z), 2β, 5α]-(±)-7-[5-[[(1,1′-Biphenyl)-4-yl]methoxy]-3-oxo-2-(4-thiomorpholinyl) cyclopentyl]-4-heptenoic acid, from Intermediate 12p. Purification by chromatography using 7:3 ER-isopentane as eluent. IR (CHBr$_3$) 3500, 1740, 1705 cm$^{-1}$. TLC ER R$_f$ 0.45

(g) [1α(Z), 2β, 5α]-(±)-7-[5-[[4′-Methoxy(1,1′-biphenyl)-3-yl]methoxy]-2-(4-morpholinyl)-3-oxocyclopentyl]-4-heptenoic acid, from Intermediate 12y. Purification by chromatography using 4:1 EA-PE (b.p. 60°–80°) as eluent. IR (CHBr$_3$) 3500, 1740, 1710 cm$^{-1}$. TLC 4:1 EA-PE (b.p. 60°–80°) Rf 0.44.

EXAMPLE 2

[1α(Z),2β,5α]-(±)-Methyl 7-[5-[[(1,1′-Biphenyl)-4-yl]methoxy]-2-(4-morpholinyl)-3-oxocyclopentyl]-4-heptenoate To a cold (−60°), stirred solution of oxalyl chloride (0.144 ml) in dry CH$_2$Cl$_2$ (20 ml) was added DMSO (0.133 ml). The solution was stirred for 15 min, when a solution of Intermediate 14 (0.37 g) in dry CH$_2$Cl$_2$ (20 ml) was added. After stirring for 2h, triethylamine (1.04 ml) in dry CH$_2$Cl$_2$ (5 ml) was added and the temperature then allowed to rise to ambient over 0.75h. ER was then added and the mixture washed with 8% NaHCO$_3$ solution. The organic phase was separated, dried and concentrated, and the residue chromatographed on silica. Elution with 3:1 ER-isopentane gave the title compound as an oil (0.23 g). I.R. (CHBr$_3$) 1730 cm$^{-1}$. Analysis Found: C, 73.1; H, 7.0; N, 2.8 C$_{30}$H$_{37}$NO$_5$ requires: C, 73.3; H, 7.6; N, 2.9%.

EXAMPLE 3

(a) [1α(Z),2β,5α]-(±)-7-[5-[4-Methoxy(phenylmethoxy)]-2-(4-morpholinyl)-3-oxocyclopentyl]-4-heptenoic acid, compound with chloroform (3:1)

To a solution of Intermediate 12c) (0.18 g) in acetone (10 ml) at −5° was added 'hyflo' (0.7 g) followed by Jones reagent (2.67 M, 0.36 ml). The temperature was allowed to rise to 5° during 45 min when isopropanol (1 ml) was added. After 5 min the mixture was filtered and the solid washed thoroughly with ER. The combined organic layers were washed with pH 6.5 phosphate buffer (2×20 ml), dried and concentrated. Purification by chromatography using 98:2 CHCl$_3$-methanol as eluent gave the title compound as an oil (0.06 g). IR (CHBr$_3$) 3500, 1740, 1710 cm$^{-1}$ TLC 98:2 CHCl$_3$-methanol Rf 0.4

The following compounds were prepared using a similar procedure:

(b) [1α(Z),2β,5α]-(±)-7-[5-[[4′-Chloro(1,1′-biphenyl)-4-yl]methoxy]-2-(4-morpholinyl)-3-oxocyclopentyl]-4-heptenoic acid, from Intermediate 12h Purification by chromatography using 99:1 CHCl$_3$-methanol as eluent. IR (CHBr$_3$) 3490, 1740, 1705 cm$^{-1}$ Analysis found: C, 67.7; H, 6.6; N, 2.8. C$_{29}$H$_{34}$ClNO$_5$ requires: C, 68.0; H, 6.7; N, 2.8%.

(c) [1α(Z),2β,5α]-(±)-7-[2-(4-Morpholinyl)-3-oxo-5-(2-propenyloxy)cyclopentyl]-4-heptenoic acid, from Intermediate 12i. Purification by chromatography using 4:1 ER-PE (b.p. 60°–80°) as eluent. IR (CHBr$_3$) 3500, 1735, 1705 cm$^{-1}$. TLC 4:1 ER-PE (b.p. 60°–80°) Rf 0.28.

(d) [1α(Z),2β,5α]-(±)-7-[2-(4-Morpholinyl)-3-oxo-5-[(4-thien-2-yl)phenylmethoxy]cyclopentyl]-4-heptenoic acid, compound with piperazine (2:1), from Intermediate 12k. The acid was purified by chromatography using 1:99 methanol-CHCl$_3$ as eluent. The title compound (140 mg) precipitated from a solution of the acid (200 mg) and piperazine (100 mg) in ER. Crystallisation from EA gave material of m.p. 115° (dec). IR (CHBr$_3$) 1740 cm$^{-1}$. TLC ER Rf 0.7.

(e) [1α(Z),2β,5α]-(±)-7-[2-(4-Morpholinyl)-3-oxo-5-[[(1,1′:4′,1″-terphenyl)-4-yl]methoxy]cyclopentyl]-4-heptenoic acid, m.p. 105° (dec) from Intermediate 12l). Purification initially by chromatography using ether as eluent and then by crystallisation from ER-isopentane at 0°. TLC 9:1 ER-methanol Rf 0.23.

(f) [1α(E),2β,5α]-(±)-7-[5-[[4′-Methyl(1,1′biphenyl)-4-yl]methoxy]-2-(4-morpholinyl)-3-oxocyclopentyl]-4-heptenoic acid, m.p. 80°–85° from Intermediate 25a. Purification initially by chromatography using ER as eluent and then by crystallisation from ER-isopentane at −20°

Analysis Found: C, 73.1; H, 7.7; N, 2.8. C$_{30}$H$_{37}$NO$_5$ requires: C, 73.3; H, 7.6; N, 2.9%.

(g) [1α(E),2β,5α]-(±)-7-[5-[[(1,1′-Biphenyl)-4-yl]methoxy]-2-(4-morpholinyl)-3-oxocyclopentyl]-4-heptenoic acid, m.p. 103°–105° from Intermediate 25b. Purification initially by chromatography using ER as eluent and then by crystallisation from ER at −20°.

Analysis Found: C, 72.8; H, 7.7; N, 3.0. $C_{29}H_{35}NO_5$ requires: C, 72.9; H, 7.4; N, 2.9%.

(h) [1α(Z),2β,5α]-(±)-9-[5-[[(1,1'-Biphenyl)-4-yl]methoxy]-2-(4-morpholinyl)-3-oxocyclopentyl]-6-nonenoic acid, m.p. 83°-84° from Intermediate 12m. Purification initially by chromatography using ER as eluent and then by crystallisation from ER-isopentane.

Analysis Found: C, 73.3; H, 7.7; N, 2.8. $C_{31}H_{39}NO_5$ requires: C, 73.6; H, 7.8; N, 2.8%.

(i) [1α(Z),2β,5α(E)]-(±)-7-[2-(4-Morpholinyl)-3-oxo-5-[(3-phenyl-2-propenyl)oxy]cyclopentyl]-4-heptenoic acid, m.p. 74.5°-76° from Intermediate 12o. Purification by chromatography using ER as eluent.

Analysis Found: C, 70.3; H, 7.9; N, 3.3. $C_{25}H_{33}NO_5$ requires: C, 70.2; H, 7.8; N, 3.3%.

(j) [1α(Z),2β,5α]-(±)-7-[5-[[4'-Methyl(1,1'-biphenyl)-4-yl]methoxy]-3-oxo-2-(4-thiomorpholinyl)cyclopentyl]-4-heptenoic acid, S-dioxide, from Intermediate 12r. Purification by chromatography using 98:2 ER-methanol as eluent. IR (CHBr$_3$) 3500, 1740, 1710 cm$^{-1}$.

Analysis Found: C, 66.5; H, 7.1; N, 2.2; $C_{30}H_{37}NO_6S$ requires: C, 66.8; H, 6.9; N, 2.6%.

(k) [1α(Z),2β,5α]-(±)-7-[3-Oxo-5-[4-(phenylmethyl)phenylmethoxy]-2-(4-thiomorpholinyl)cyclopentyl]-4-heptenoic acid, S-dioxide, m.p. 126.5°-128° (dec) from Intermediate 12s. Purification by chromatography using ER as eluent. TLC 95:5 ER-methanol Rf 0.46.

(l) [1α(Z),2β,5α]-(±)-7-[5-[[(1,1'-Biphenyl)-4-yl]methoxy]-3-oxo-2-(4-thiomorpholinyl)cyclopentyl]-4-heptenoic acid, S-dioxide, from Intermediate 12t. Purification by chromatography using 98:2 ER-methanol as eluent. IR (CHBr$_3$) 3480, 1743, 1710 cm$^{-1}$.

Analysis Found: C, 66.0; H, 6.7; N, 2.6; $C_{29}H_{35}NO_6S$ requires: C, 66.3; H, 6.7; N, 2.7%.

(m) [1α(Z),2β,5α]-(±)-7-[5-[[(1,1'-Biphenyl)-4-yl]methoxy]-2-(hexahydro-1,4-oxazepin-4-yl-3-oxocyclopentyl]-4-heptenoic acid, from Intermediate 12u. Purification by chromatography using ER as eluent. IR (Neat) 3500-2500 (br), 1740, 1710 cm$^{-1}$. TLC ER Rf 0.47.

(n) [1α(Z),2β,5α]-(±)-7-[5-[3-[(1,1'-Biphenyl)-4-yl]propoxy]-2-(4-morpholinyl)-3-oxocyclopentyl]-4-heptenoic acid, from Intermediate 12w. Purification by chromatography using ER as eluent. IR (Neat) 3700-2200 (br), 1740, 1712 cm$^{-1}$. TLC ER Rf 0.25.

(o) [1α(Z),2β,5α]-(±)-7-[5-[[3'-Methoxy(1,1'-biphenyl)-4-yl]methoxy]-2-(4-morpholinyl)-3-oxocyclopentyl]-4-heptenoic acid, from Intermediate 12x. Purification by chromatography using ER as eluent. IR (CHBr$_3$) 3500, 1740, 1710 cm$^{-1}$. TLC ER Rf 0.2.

(p) [1α(Z),2β,5α]-(±)-7-[5-Decyloxy-2-(4-morpholinyl)-3-oxocyclopentyl]-4-heptenoic acid from Intermediate 12z. Purification by chromatography using 4:1 ER-PE as eluent. IR (CHBr$_3$) 3500, 1740, 1710 cm$^{-1}$. TLC (SiO$_2$) 4:1 ER-PE R$_f$ 0.21.

EXAMPLE 4

(a) [1α(Z),2β,5α]-(±)-7-[5-(4-Cyclohexylphenylmethoxy)-2-(4-morpholinyl)-3-oxocyclopentyl]-4-heptenoic acid A stirred solution of oxalyl chloride (0.612 ml) in dry toluene (5 ml) under nitrogen at −60° was treated dropwise with a solution of dry DMSO (0.5 ml) in dry toluene (5 ml) and the mixture stirred for 10 min. Simultaneously chlorotrimethylsilane (0.24 ml) was added dropwise to a solution of Intermediate 12e, (0.84 g) and triethylamine (0.264 ml) in dry toluene (10 ml) under nitrogen. This mixture was swirled for 5 min before being added dropwise to the above reaction mixture. The resulting solution was stirred at −60° for 15 min and then quenched with triethylamine (2.8 ml). The mixture was allowed to warm to 0°, poured into aqueous KH$_2$PO$_4$ (3.5 g in 200 ml water) and extracted with EA (4×50 ml). The combined organic extracts were washed with pH 6.5 phosphate buffer (2×20 ml), dried and concentrated. The residue was purified by chromatography on silica using 3:1 ER-PE as eluent to give the title compound as a gum (56 mg). IR (CHBr$_3$) 3500, 1740, 1710 cm$^{-1}$. TLC 80:1 ER-acetic acid Rf 0.39.

The following compounds were prepared using a similar procedure:

(b) [1α(Z),2β,5α]-(±)-7-[2-(4-Morpholinyl)-3-oxo-5-(pentyloxy)cyclopentyl]-4-heptenoic acid, compound with piperazine (2:1), from Intermediate 12f. Purification of the acid by chromatography using ER as eluent. The title compound (212 mg) crystallised from a solution of the acid (271 mg) and piperazine (45 mg) in ER (10 ml) to give material of m.p. 99°-102.5° (dec).

Analysis Found: C, 64.9; H, 9.5; N, 6.8. $C_{23}H_{40}N_2O_5$ requires: C, 65.1; N, 9.5; N, 6.6%.

(c) [1α(Z),2β,5α]-(±)-7-[2-(4-Morpholinyl)-3-oxo-5-[4-(phenylmethyl)phenylmethoxy]cyclopentyl]-4-heptenoic acid, compound with piperazine (2:1), m.p. 107-108 from Intermediate 12g.

Analysis Found: C, 71.6; H, 7.9; N, 5.2 $C_{32}H_{42}N_2O_5$ requires: C, 71.9; H, 7.9; N, 5.2%.

(e) [1α(Z),2β,5α]-(±)-7-[5-[[(1,1'-Biphenyl)-4-yl]methoxy]-3-oxo-2-(1-piperidinyl)cyclopentyl]-4-heptenoic acid, compound with piperazine (2:1), m.p. 91°-94° (dec) from Intermediate 33b. IR (CHBr$_3$) 1738 cm$^{-1}$.

(f) [1α(Z),2β,5α]-(±)-7-[5-[[4'-Methoxy(1,1'-biphenyl)-4-yl]methoxy]-3-oxo-2-(4-thiomorpholinyl)-cyclopentyl]-4-heptenoic acid, S-dioxide, from Intermediate 12q. Purification by chromatography using 98:2 ER-methanol as eluent. TLC 95:5 ER-methanol Rf 0.46. IR (CHBr$_3$) 3480, 1740, 1710 cm$^{-1}$.

(g) [1α(Z),2β,5α]-(±)-7-[5-[[4'-Methoxy(1,1'-biphenyl)-4-yl]methoxy]-3-oxo-2-(1-piperidinyl)cyclopentyl]-4-heptenoic acid, compound with piperazine (2:1), m.p. 68°-76° (dec) from Intermediate 12v. IR (CHBr$_3$) 1740 cm$^{-1}$.

EXAMPLE 5

[1α(Z),2β,5α]-(±)-7-[5-[[4'-Methyl(1,1'-biphenyl)-4-yl]methoxy]-2-(4-morpholinyl)-3-oxocyclopentyl]-4-heptenoic acid A solution of Intermediate 18 (928 mg) in acetone (30 ml) was stirred with Jones reagent (2.67 M; 1.5 ml) at −5° to −3° for 40 min. Isopropanol (1.5 ml) was added and after stirring for 5 min, the mixture was poured into pH 6 phosphate buffer (100 ml) and extracted with ER (3×50 ml). The combined extracts were evaporated and the residue taken into ER and dried; evaporation of this ethereal solution gave a foam (840 mg) which was purified by chromatography on acid-washed silica gel (85 g) using ER as eluent. Crystallisation from ER-isopentane at 0° gave the title compound (0.26 g) of m.p. 98°-102°. IR (CHBr$_3$) 3500, 1740, 1710 cm$^{-1}$.

Analysis Found: C, 72.9; H, 7.6; N, 2.9. $C_{30}H_{37}NO_5$ requires: C, 73.3; H, 7.6; N, 2.9%.

EXAMPLE 6

[1α(Z),2β,5α]-(±)-7-[5-[[4'-Methoxy(1,1'-biphenyl)-4-yl]methoxy]-2-(4-morpholinyl)-3-oxocyclopentyl]-4-heptenoic acid, compound with piperazine (2:1)

Jones reagent (0.883 ml, 2.7 M) was added to Intermediate 21 (600 mg) in acetone (25 ml) at −10° and stirred for 45 min at 10°. The mixture was neutralised by (25 ml) dropwise addition of 2 N aqueous $Na_2CO_3$ and then poured into $Na_2HPO_4/KH_2PO_4$ buffer solution (pH 6). The mixture was extracted with $CH_2Cl_2$ (3×50 ml) and the combined extracts dried, filtered and evaporated. The residue was chromatographed on acid washed silica using 1:1 through to 3:1 ER-PE (b.p. 60°–80°) as eluent to give an oil, which was dissolved in ER and treated with an excess of piperazine in ER to give the title compound as a solid (0.12 g), m.p. 116°–117° (dec).

Analysis Found: C, 69.7; H, 7.6; N, 5.2 $C_{32}H_{42}N_2O_6$ requires: C, 69.8; H, 7.7; N, 5.1%.

EXAMPLE 7

[1α(Z),2β,5α]-(±)-7-[5-[[(1,1'-Biphenyl)-4-yl]methoxy]-2-(4-morpholinyl)-3-oxocyclopentyl]-4-heptenoic acid, compound with piperazine (2:1), hemihydrate To a solution of Example 1a (0.37 g) in dry ER (20 ml) was added piperazine (0.037 g) in dry ER (4 ml). The ER was decanted off and the residue crystallised from $CH_2Cl_2$-isopentane to give the title compound (0.2 g) m.p. 113°–114°.

Analysis found: C, 70.9; H, 7.7; N, 5.4. $C_{31}H_{40}N_2O_5.\frac{1}{4}$ $H_2O$ requires: C, 70.9; H, 7.7; N, 5.4%.

EXAMPLE 8

[1α(Z),2β,5α]-(±)-7-[5-[[(1,1'-Biphenyl)-4-yl]methoxy]-2-(4-morpholinyl)-3-oxocyclopentyl]-4-heptenoic acid, calcium (2+) (2:1), monohydrate Aqueous 0.2 N.NaOH (2 ml) was added dropwise with stirring to a solution of Example 1a (0.25 g) in aqueous acetone (1:1), 10 ml) at room temperature until the pH reached 7.8. 7.2% w/v $CaCl_2$ (1 ml) was then added followed by water (10 ml) and stirring continued for 2h. The solid was filtered off, washed with water (5 ml) followed by ER (10 ml) and dried (35°/0.05 mmHg/7h) to afford the title compound (0.163 g), m.p. 132°–134°.

Analysis Found: C, 69.1; H, 6.8; N, 2.6; Ca, 3.9. $C_{58}H_{68}N_2O_{10}Ca.H_2O$ requires: C, 68.9; H, 7.0; N, 2.8; Ca, 4.0%.

EXAMPLE 9

[1α(Z),2β,5α]-(±)-7-[5-[[(1,1'-Biphenyl)-4-yl]methoxy]-2-(4-morpholinyl)-3-oxocyclopentyl]-4-heptenoic acid, calcium (2+) (2:1), trihydrate Aqueous calcium acetate solution (0.17 g in 12 ml) was added dropwise with stirring to a solution of Example 1a (0.6 g) and $NaHCO_3$ (0.106 g) in aqueous ethanol (1:1, 24 ml). The mixture was stirred for 30 min when the solid was filtered off, washed with water (10 ml) followed by ER (5 ml) and dried (45°/200 mmHg/4h) to afford the title compound (0.56 g), m.p. 135° (dec).

Analysis Found: C, 66.2; H, 6.9; N, 2.6; Ca, 3.6. $C_{58}H_{68}N_2O_{10}Ca.3H_2O$ requires: C, 66.5; H, 6.9; N, 2.7; Ca, 3.8%.

EXAMPLE 10

[1α(Z),2β,5α]-(±)-7-[5-[[(1,1'-Biphenyl)-4-yl]methoxy]-2-(4-morpholinyl)-3-oxocyclopentyl]-4-heptenoic acid, compound with N,N-dimethylpiperazine (2:1)

A solution of Example 1a) (0.35 g) in ER (25 ml) was treated with a solution of N,N-dimethylpiperazine (0.084 g) in ER (5 ml) and the mixture was allowed to stand in the cold. The title compound was filtered off and dried (0.33 g), m.p. 106°–108°.

Analysis Found C, 71.9; H, 7.9; N, 5.1. $C_{32}H_{42}N_2O_5$ requires: C, 71.9; H, 7.9; N, 5.2%.

EXAMPLE 11

(a) [1R-[1α(Z),2β,5α]]-(−)-7-[5-[[(1,1'-Biphenyl)-4-yl]methoxy]-2-(4-morpholinyl)-3-oxocyclopentyl]-4-heptenoic acid Jones reagent (1.83 ml, 2.67 M) was added to a stirred mixture of 'hyflo' (4.8 g) and the free base of Intermediate 47a) (1.2 g) in acetone (40 ml) at 5° and stirring was continued for 40 min. Isopropanol (1.8 ml) was added dropwise and after 10 min the hyflo was removed by filtration and was washed with acetone (30 ml) and pH 5 buffer (50 ml, $KH_2PO_4$ and $Na_2HPO_4$ in water). The combined filtrates were, evaporated in vacuo at 10°–15° to remove most of the acetone. The residue was diluted with pH 5 buffer (25 ml) and extracted with ER (4×50 ml). The combined extracts were washed with pH 5 buffer (20 ml) and brine (20 ml), then dried and evaporated to give an oil. The oil was chromatographed on silica using ER as eluent to give a solid (0.58 g) which was recrystallised from 2:1 ER-isopentane (15 ml) to give the title compound (0.484 g), m.p. 86°–88°. $[\alpha]_D^{21.5} = -13.66°$ ($CHCl_3$).

Analysis Found: C, 72.5; H, 7.5; N, 2.7. $C_{29}H_{35}NO_5$ requires: C, 72.9; H, 7.4; N, 2.9%.

The following compound was prepared starting from Intermediate 35, in a similar manner to the preparation of the 1R compound:

(b) [1S-[1α(Z),2β,5α]]-(+)-7-[5-[[(1,1'-Biphenyl)-4-yl]methoxy]-2-(4-morpholinyl)-3-oxocyclopentyl]-4-heptenoic acid, m.p. 81°–84°.

Analysis Found: C, 72.8; H, 7.3; N, 2.7. $C_{29}H_{35}NO_5$ requires: C, 72.9; H, 7.4; N, 2.9%.

EXAMPLE 13

[1R-[1α(Z),2β,5α]]-(−)-7-[5-[[1,1'-Bisphenyl)-4-yl]methoxy]-2-(4-morpholinyl)-3-oxocyclopentyl]-4-heptenoic acid, calcium (2+) (2:1), dihydrate Aqueous calcium acetate solution (0.083 g in 4.8 ml) was added dropwise with stirring to a solution of Example 11 (0.25 g) and $NaHCO_3$ (40 mg) in aqueous ethanol (1:1, 9.6 ml). The mixture was stirred at room temperature for 2h when the solid was filtered off, washed with water and dried (20°/0.1 mmHg/20h) to afford the title compound (0.23 g), m.p. 129°–131°. $[\alpha]_D^{21} = -28.47°$ ($CHCl_3$).

Analysis Found: C, 67.4; H, 6.8; N, 2.7; Ca, 3.5. $C_{58}H_{68}N_2O_{10}Ca.2H_2O$ requires: C, 67.7; H, 7.0; N, 2.7; Ca, 3.9%.

PHARMACEUTICAL EXAMPLES

Tablets

These may be prepared by direct compression or wet granulation. The direct compression method is preferred but may not be suitable in all cases as it is depen-

| A. | Direct Compression | mg/tablet |
|---|---|---|
| | Active ingredient | 100.00 |
| | Microcrystalline Cellulose B.P.C. | 298.00 |
| | Magnesium Stearate | 2.00 |
| | Compression Weight | 400.00 |

The active ingredient is sieved through a 250 m$^{-6}$ sieve, blended with the excipients and compressed using 10.0 mm punches. Tablets of other strengths may be prepared by altering the compression weight and using punches to suit.

| B. | Wet Granulation | mg/tablet |
|---|---|---|
| | Active ingredient | 100.00 |
| | Lactose B.P. | 238.00 |
| | Starch B.P. | 40.00 |
| | Pregelatinised Maize Starch B.P. | 20.00 |
| | Magnesium Stearate B.P. | 2.00 |
| | Compressed Weight | 400.00 |

The active ingredient is sieved through a 250 m$^{-6}$ sieve and blended with the lactose, starch and pregelatinised starch. The mixed powders are moistened with purified water, granules are made, dried, screened and blended with the magnesium stearate. The lubricated granules are compressed into tablets as described for the direct compression formulae.

The tablets may be film coated with suitable film forming materials, e.g. methyl cellulose or hydroxylpropyl methyl cellulose using standard techniques. Alternatively the tablets may be sugar coated.

| Capsules | mg/capsule |
|---|---|
| Active ingredient | 100.00 |
| *STA-RX 1500 | 99.00 |
| Magnesium Stearate B.P. | 1.00 |
| Fill Weight | 200.00mg |

The active ingredient is sieved through a 250 m$^{-6}$ sieve and blended with the other materials. The mix is filled into No. 2 hard gelatin capsules using a suitable filling machine. Other doses may be prepared by altering the fill weight and if necessary changing the capsule size to suit.

| Inhalation Cartridges | /cartridge |
|---|---|
| Active ingredient (micronised) | 3 mg |
| Lactose B.P. to | 25 mg |

The active ingredient is micronised so that the majority of the particles are between 1 m$^{-6}$ and 5 m$^{-6}$ in longest dimensions and none are greater than 10 m$^{-6}$. The active ingredient is then blended with the lactose and the mix is filled into No. 3 hard gelatin capsules using a suitable filling machine.

| Suspensions | mg/5ml dose |
|---|---|
| Active ingredient | 100.0 |
| Aluminium monostearate | 75.0 |
| Sucrose (powdered) | 125.0 |
| Flavour | as |
| Colour | required |
| Fractionated coconut oil to | 5.00ml. |

The aluminium monostearate is dispersed in about 90% of the fractionated coconut oil. The resulting suspension is heated to 115° C. while stirring and then cooled. The flavour and colour are added and the active ingredient and sucrose are suitably dispersed. The suspension is made up to volume with the remaining fractionated coconut oil and mixed.

| Injection for Intravenous Administration | |
|---|---|
| Active ingredient | 50 mg |
| Suitable vehicle to | 5ml. |

A sterile presentation of the active ingredient in an ampoule or vial together with an ampoule containing a suitable vehicle. The former may be prepared by (a) filling sterile material into vials under aseptic conditions (b) freeze drying a sterile solution of the active ingredient under aseptic conditions.

The vehicle may be (a) Water for Injections B.P. (b) Water for Injections B.P. containing: (1) Sodium chloride to adjust the tonicity of the solution and/or (2) buffer salts or dilute acid or alkali to facilitate solution of the active ingredient.

The vehicle is prepared, clarified and filled into appropriate sized ampoules sealed by fusion of the glass. The vehicle is sterilised by heating in an autoclave using one of the acceptable cycles.

We claim:

1. Compounds of the general formula (1)

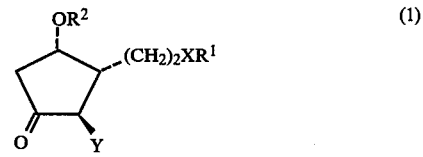

wherein

X is cis or trans -CH=CH-;

R$^1$ is straight or branched C$_{1-7}$ alkyl bearing as a terminal substituent -COOR$^3$ where R$^3$ is a hydrogen atom, C$_{1-6}$ alkyl or C$_{7-10}$ aralkyl;

Y represents a saturated heterocyclic amino group which has 5 to 7 ring members and (a) optionally contains in the ring -O-, -S-, -SO$_2$-, -NR$^4$ (where R$^4$ is a hydrogen atom, C$_{1-7}$ alkyl or aralkyl having a C$_{1-4}$ alkyl portion; and (b) is optionally substituted by one or more C$_{1-4}$ alkyl groups;

R$^2$ is (i) C$_{2-4}$ alkanoyl; (ii) C$_{3-6}$ alkenyl, optionally substituted by phenyl (the phenyl being optionally substituted by C$_{1-4}$ alkyl, C$_{1-4}$ alkoxy, halogen, C$_{5-7}$ cycloalkyl or phenyl (C$_{1-4}$) alkyl), biphenyl (optionally substituted by C$_{1-4}$ alkyl, C$_{1-4}$ alkoxy or halogen), or naphthyl; (iii) C$_{1-12}$ alkyl; (iv) C$_{1-5}$ alkyl substituted by (a) phenyl, (b) biphenyl (optionally substituted by phenyl or one or two C$_{1-4}$ alkyl, C$_{1-4}$ alkoxy, halogen substitutuents), or (c) naphthyl (optionally substituted by C$_{1-4}$ alkyl, C$_{1-4}$ alkoxy or halogen);

and the physiologically acceptable salts and the solvents thereof.

2. Compounds as claimed in claim 1 in which Y is morpholino, dioxothiamorpholino, homomorpholino, thiamorpholino or piperidino.

3. Compounds as claimed in claim 1 in which X is cis -CH=CH-.

4. Compounds as claimed in claim 1 in which $R^1$ is -$(CH_2)_2COOR^3$ where $R^3$ is a hydrogen atom or $C_{1-3}$ alkyl.

5. Compounds as claimed in claim 1 in which $R^2$ is phenyl ($C_{1-3}$) alkyl in which the phenyl group substituted by $C_{1-3}$ alkylthio, thienyl, or phenyl (optionally substituted by $C_{1-3}$ alkyl, $C_{1-3}$ alkoxy, halogen or phenyl); or cinnamyl.

6. Compounds as claimed in claim 5 in which $R^2$ is phenyl ($C_{1-3}$) alkyl in which the phenyl group is substituted by phenyl, $C_{1-3}$ alkylphenyl, $C_{1-3}$ alkoxyphenyl or halophenyl; or cinnamyl.

7. Compounds as claimed in claim 1 in which:
X is cis -CH=CH-;
$R^1$ is -$(CH_2)_2COOH$;
Y is morpholino or piperidino;
$R^2$ is phenyl ($C_{1-3}$) alkyl in which the phenyl group is substituted by phenyl, $C_{1-3}$ alkylphenyl, $C_{1-3}$ alkoxyphenyl or halophenyl; or cinnamyl.

and the physiologically acceptable salts and solvates thereof.

8. Compounds as claimed in claim 1 in which the carbon atom carrying the —$(CH_2)_2XR^1$ group is in the R-configuration.

9. Compounds as claimed in claim 7 in which Y is morpholino and $R_2$ is 1,1'-biphenylmethyl; 1,1'-biphenylmethyl substituted in the-para position by methyl, methoxy or chloro or in the meta-position by methoxy; 1,1'-biphenylpropyl; or cinnamyl.

10. [1α(Z),2β,5α]-(±)-7-[5-[[(1,1'-biphenyl)-4-yl]methyoxy]-2-(4-morpholinyl)-3-oxocyclopentyl]-4-heptenoic acid or a physiologically acceptable salt or solvate thereof.

11. [1R[1α(Z),2β,5α]]-(−)-7-[5-[[(1,1'-biphenyl)-4-yl]methoxy]-2-(4-morpholinyl)-3-oxocyclopentyl]-4-heptenoic acid or a physiologically acceptable salt or solvate thereof.

12. The calcium, piperidine, piperazine or N,N-dimethylpiperazine salt of the compound of claim 10 or 11.

13. The calcium salts of the compounds claimed in claims 10 or 11.

14. A pharmaceutical composition comprising an antithrombotic or anti-asthmatic effective amount of a compound as claimed in claim 1 together with one or more pharmaceutical carriers.

* * * * *

UNITED STATES PATENT AND TRADEMARK OFFICE
CERTIFICATE OF CORRECTION

PATENT NO. : 4,342,756  
DATED : August 3, 1982  
INVENTOR(S) : Collington, et al.

Page 1 of 2

It is certified that error appears in the above-identified patent and that said Letters Patent is hereby corrected as shown below:

Column 3, line 57, "which an added" should be -- with an added --

Column 23, line 25, "endo,syn)-($\pm$)-[[1,1'-" should be -- (endo,syn)-($\pm$)-5-[[1,1' --

Column 23, line 48, (4.33ml), 612 M) should be -- (4.33ml, 612 M) --

Column 23, line 65, "tyl[4-heptenoate" should be -- tyl]-4-heptenoate --

Column 25, line 28, "[3.2.0]heptan6-one" should be -- [3.2.0]heptan-6-one --

Column 26, line 6, "y]8-" should be -- y]-8- --

Column 26, line 26, "$CH_3Cl_2$" should be -- $CH_2Cl_2$ --

Column 26, line 40, "y]3-hydroxy-" should be -- y]-3-hydroxy- --

Column 26, line 49, "was" second occurrence should be -- with --

Column 28, line 8, there should be no "(a)

Column 28, line 19, there should be -- "(a)" -- at beginning of line

Column 42, lines 11 and 12, "methyoxy" should be -- methoxy --.

UNITED STATES PATENT AND TRADEMARK OFFICE
CERTIFICATE OF CORRECTION

PATENT NO. : 4,342,756

DATED : August 3, 1982

INVENTOR(S) : Collington, et al.

Page 2 of 2

It is certified that error appears in the above-identified patent and that said Letters Patent is hereby corrected as shown below:

Column 38, line 48, "Bisphenyl" should be -- Biphenyl --

Column 41, lines 1 and 2, "solvents" should be -- solvates --

Column 40, line 64, after phenyl," add: -- [optionally substituted by halogen, hydroxy, $C_{1-6}$ alkyl, $C_{1-6}$ alkoxy, $C_{1-4}$ hydroxyalkoxy, trifluoromethyl, cyano, aryloxy, $C_{5-7}$ cycloalkyl, aralkoxy, dimethylaminomethyl, carboxamido ($-CONH_2$), thiocarboxamido ($-CSNH_2$), $C_{1-4}$ alkanoyl, $-NR^5R^6$ (where $R^5$ and $R^6$ are the same or different and are each a hydrogen atom or $C_{1-4}$ alkyl, or where $-NR^5R^6$ is a saturated heterocyclic amino group as defined above for Y), $C_{1-3}$ alkylthio, $C_{1-3}$ alkylsulphinyl, $C_{1-3}$ alkylsulphonyl, phenylalkyl having a $C_{1-3}$ alkyl portion, aminosulphonyl, $C_{1-3}$ alkanoylaminosulphonyl, phenylsulphonyl (the phenyl portion being optionally substituted by $C_{1-3}$ alkyl or $C_{1-3}$ alkoxy), nitro, or thienyl], --

Signed and Sealed this

Second Day of April 1985

[SEAL]

Attest:

DONALD J. QUIGG

Attesting Officer

Acting Commissioner of Patents and Trademarks